(12) United States Patent
Wang et al.

(10) Patent No.: US 7,078,591 B2
(45) Date of Patent: Jul. 18, 2006

(54) CYCLIN-DEPENDENT KINASE INHIBITORS AS PLANT GROWTH REGULATORS

(75) Inventors: Hong Wang, Saskatoon (CA); Larry C. Fowke, Saskatoon (CA); William L. Crosby, Saskatoon (CA)

(73) Assignees: Her Majessty the Queen in right of Canada, as represented by the Minister of Natural Resources, Saskatoon (CA); University of Saskatchewan, Saskatoon (CA); The Natural Research Council of Canada, Ottawa (CA)

( * ) Notice: Subject to any disclaimer, the term of this patent is extended or adjusted under 35 U.S.C. 154(b) by 433 days.

(21) Appl. No.: 09/733,507

(22) Filed: Dec. 8, 2000

(65) Prior Publication Data

US 2001/0025379 A1    Sep. 27, 2001

Related U.S. Application Data

(63) Continuation-in-part of application No. PCT/CA99/00532, filed on Jun. 8, 1999.

(51) Int. Cl.
*C12N 15/82* (2006.01)
*C12N 15/29* (2006.01)

(52) U.S. Cl. ...................................... 800/290; 435/468
(58) Field of Classification Search ................ 800/290, 800/298; 435/468, 320.1, 419; 536/23.6
See application file for complete search history.

(56) References Cited

U.S. PATENT DOCUMENTS 5,750,862 A * 5/1998 John ........................... 800/320
6,087,175 A * 7/2000 John ........................... 435/419

FOREIGN PATENT DOCUMENTS

WO    WO 97 26327    7/1997
WO    WO 99 14331    3/1999

OTHER PUBLICATIONS

Peter M. The regulation of cyclin-dependent kinase inhibitors (CKIs). Prog Cell Cycle Res. 1997;3:99-108.*
Sun Y. et al Characterization of maize (Zea mays L.) Wee1 and its activity in developing endosperm. Proc Natl Acad Sci U S A Mar. 30, 1999;96(7):4180-5.*
Mazur X et al. Higher productivity of growth-arrested Chinese hamster ovary cells expressing the cyclin-dependent kinase inhibitor p. 27. Biotechnol Prog. Sep.-Oct. 1998;14(5):705-13.*
Di Cunto F et al. (Inhibitory function of p21Cip1/WAF1 in differentiation of primary mouse keratinocytes independent of cell cyc control. Science. May 15, 1998;280(5366):1069-72.*
Harper J.W. Cyclin dependent kinase inhibitors. Cancer Surv. 1997;29:91-107.*
Braun SE et al. A positive effect of p21cip1/waf1 in the colony formation from murine myeloid progenitor cells as assessed by retroviral-mediated gene transfer. Blood Cells Mol Dis. Jun. 1998;24(2):138-48.*
Segers G. et al. The Arabidopsis cyclin-dependent kinase gene cdc2bAt is preferentially expressed during S and G2 phases of the cell cycle. Plant J. Oct. 1996;10(4):601-12.*
Dahl M. et al. The D-type alfalfa cyclin gene cycMs4 complements G1 cyclin-deficient yeast and is induced in the G1 phase of the cell cycle. Plant Cell. Nov. 1995;7(11)1847-57.*
Margulis M (Biodiversity: molecular biological domains, symbiosis and kingdom origins. Biosystems. 1992;27(1):39-51.*
Wang et al., "*Arabidopsis thaliana* cyclin-dependent kinase inhibitor protein (ICK1) mRNA, complete cds." EMBL Accession No. U94772, Apr. 29, 1997.
Wang et al., "A plant cyclin-dependent kinase inhibitor gene," *Nature*, 386:451-452, Apr. 3, 1997.
Doerner et al., "Control of root growth and development by cyclin expression," *Nature*, 380:520-523, Apr. 11, 1996.
Doonan, "Plant growth: roots in the cell cycle," *Current Biology*, 6(7):788-789, Jul. 1, 1996.
Fountain, "*Chenopodium rubrum* G1 cyclin-dependent kinase inhibitor mRMA, complete cds." EMBL Accession No. AJ002173, Nov. 27, 1997.
Cho Jeong et al., "The size and shape of plant leaf is controlled by cyclin D1 kinase and its novel inhibitor p22ack1," *FASEB J.* 15(4):A517, Mar. 7, 2001.
Cockcroft et al., "Cyclin D control of growth rate in plants," *Nature* 405:575-579, Jun. 1, 2000.

(Continued)

*Primary Examiner*—Cynthia Collins
(74) *Attorney, Agent, or Firm*—Klarquist Sparkman, LLP

(57) ABSTRACT

Methods for using cyclin-dependent kinase (CDK) inhibitor genes, or anti-sense constructs complementary to such genes, to modify the growth and development of plant cells and organs are disclosed. Also provided are methods of modifying the development of plant cells and plants by transforming plant cells with nucleic acids encoding cyclin-dependent kinase inhibitor polypeptides, or anti-sense constructs complementary to such nucleic acids, to produce transformed plant cells, and then culturing the plant cells or regenerating a plant under conditions wherein the cyclin-dependent kinase inhibitor, or the anti-sense construct, is expressed. A variety of CDK inhibitor genes, and corresponding anti-sense constructs, are disclosed for use in a variety of plants. The nucleic acid encoding the cyclin-dependent kinase inhibitor may be operably linked to a tissue-specific promoter. Other provided aspects are modified transgenic plants and plant tissues. Also provided are methods of identifying nucleic acids that encode cyclin-dependent kinase inhibitors that are active in plants to modify the development of the plant.

16 Claims, 8 Drawing Sheets

OTHER PUBLICATIONS de Boer and Murray, "Control of plant growth and development through manipulation of cell-cycle genes," *Curr. Opin. Biotech.* 11:138-145, 2000.

Genschik et al., "Cell Cycle-Dependent Proteolysis in Plants: Identification of the Destruction Box Pathway and Metaphase Arrest Produced by the Proteasome Inhibitor MG132," *Plant Cell* 10:2063-2075, Dec. 1998.

Mironov et al., "Cyclin-Dependent Kinases and Cell Division in Plants—The Nexus," *Plant Cell* 11:509-521, Apr. 1999.

Riou-Khamlichi et al., "Cytokinin Activation of *Arabidopsis* Cell Division Through a D-Type Cyclin," *Science* 283:1541-1544, Mar. 5, 1999.

Wang et al., "Expression of the plant cyclin-dependent kinase inhibitor ICK1 affects cell division, plant growth and morphology," *Plant J.* 24(5):613-623, 2000.

Alberts B, Bray D, Lewis J, Raff M, Roberts K, Watson JD (1983) Molecular Biology of the Cell. Garland Publishing: New York, pp. 1139-1142.

Bell MH, Halford NG, Ormrod JC, Francis D (1993) Tobacco plants transformed with cdc25, a mitotic inducer gene from fission yeast. Plant Mol Biol 23: 445-451.

Brock TG, Kaufman PB (1991) Growth regulators: an account of hormones and growth regulation. In Growth and Development, Plant Physiology—A Treatise. vol. 10. Academic Press: San Diego, pp. 277-340.

Colasanti J, Cho S-O, Wick S, Sundaresan V (1993) Localization of the functional $p34^{cdc2}$ homolog of maize in root tip and stornatal complex cells: association with predicted vision sites. Plant Cell 5: 1101-1111.

De Veylder L, Segers G, Glab N, Casteels P, Van Montagu M, Inzé D (1997) The *Arabidopsis* Cks1At protein binds the cyclin-dependent kinases Cdc2aAt and Cdc2bAt. FEBS Lett 412: 446-452.

Doonan J, Fobert P (1997) Conserved and novel regulators of the plant cell cycle. Curr Opin Cell Biol 9:824-830.

Evans, M.L. (1984) Functions of hormones at the cellular level of organization. In Hormonal Regulation of Development II. Encyclopedia of Plant Physiology, New Series, vol. 10 (Scott T. K. ed.). Berlin: Springer-Verlag, pp. 23-79.

Ferreira PCG, Hemerly AS, de Almeida Engler J, Van Montagu M, Engler G, Inzé D (1994) Developmental expression of the *Arabidopsis* cyclin gene cyc1At. Plant Cell 6: 1763-1774.

Ferreira PCG, Hemerly AS, Villarroel R, Van Montagu M, Inzé D (1991) The *Arabidopsis* functional homolog of the $p34^{cdc2}$ protein kinase. Plant Cell 3: 531-540.

Francis D, Halford NG (1995) The plant cell cycle. Physiol Plant 93: 365-374.

Gorst JR, John PCL, Sek FJ (1991) Levels of $p34^{cdc2}$-like protein in dividing, differentiating and dedifferentiating cells of carrot. Planta 185: 304-310.

Grafi G, Larkins BA (1995) Endoreduplication in maize endosperm: involvement of M phase-promoting factor inhibition and induction of S phase-related kinases. Science 269: 1262-1264.

Hagege D (1993) Proto-oncogenes in plants: widespread conserved genes for which roles? Plant Physiol Biochem 31: 621-629.

Harper JW, Elledge SJ (1996) Cdk inhibitors in development and cancer. Curr Opin Genet Dev 6: 56-64.

Hemerly, A.S. et al. (1999) Cell Cycle Control and Plant Morhogenesis: is There an Essential Link, Bio Essays, vol. 21, pp. 29-37.

Hemerly AS, Ferreira PCG, de Almeida Engler J, Van Montagu M, Engler G, Inzé D (1993) cdc2a expression in *Arabidopsis thaliana* is linked with competence for cell division. Plant Cell 5: 1711-1723.

Hemerly A, de Almeida Engler J, Bergounioux C, Van Montagu M, Engler G, Inzé D, Ferreira P (1995) Dominant negative mutants of the Cdc2 kinase uncouple cell division from iterative plant development. EMBO J 14: 3925-3936.

Hindley J, Phear GA (1984) Sequence of the cell division gene CDC2 from *Schizosaccharomyces pombe:* patterns of splicing and homology to protein kinases. Gene 31: 129-134.

Hirayama T, Imajuku Y, Anai T, Matsui M, Oka A (1991) Identification of two cell-cycle-controlling cdc2 gene homologs in *Arabidopsis thaliana*. Gene 105: 159-165.

Hirt H (1996) In and out of the plant cell cycle. Plant Molec Biol 31: 459-464.

Jacobs T (1997) Why do plant cells divide? Plant Cell 9: 1021-1029.

Jacobs TW (1995) Cell cycle control. Annu Rev Plant Physiol Plant Mol Biol 46: 317-339.

Kaplan DR, Hagemann W (1991) The relationship of cell and organism in vascular plants. BioScience 41: 693-703.

John PCL, Zhang K, Dong C, Diederich L, Wightman F (1993) $p34^{cdc2}$ related proteins in control of cell cycle progression, the switch between division and differentiation in tissue development, and stimulation of division by auxin and cytokinin. Aust J Plant Physiol 20: 503-526.

Lees E (1995) Cyclin-dependent kinase regulation. Curr Opin Cell Biol 7: 773-780.

Lindsey, K. and Topping, J. (1998) On the Relationship Between the Plant Cell and the Plant. vol. 9, pp. 171-177.

Lorincz AT, Reed SI (1984) Primary structure homology between the product of yeast cell division control gene CDC28 and vertebrate oncogenes. Nature 307: 183-185.

Luscher B, Eisenman RN (1990) New light on Myc and Myb. Part II. Myb. Genes Dev 4: 2235-2241.

Martin C, Paz-Ares J (1997) MYB transcription factors in plants. Trends Genet 13: 67-73.

Martinez MC, Jorgensen JE, Lawton MA, Lamb CJ, Doerner PW (1992) Spatial pattern of cdc2 expression in relation to meristem activity and cell proliferation during plant development. Proc Natl Acad Sci USA 89: 7360-7364.

Meyerowitz EM (1997) Genetic control of cell division patterns in developing plants. Cell 88: 299-308.

Miao G-H, Hong Z, Verma DPS (1993) Two functional soybean genes encoding $p34^{cdc2}$ protein kinases are regulated by different plant developmental pathways Proc Natl Acad Sci USA 90: 943-947.

Mineyuki Y, Yamashita M, Nagahama Y (1991) $p34^{cdc2}$ kinase homologue in the preprophase band. Protoplasma 162: 182-186.

Mizoguchi T, Gotoh Y, Nishida E, Yamaguchi-Shinozaki K, Hayashida N, Iwasaki T, Kamada H, Shinozaki K (1994) Characterization of two cDNAs that encode MAP kinase homologues in *Arabidopsis thaliana* and analysis of the possible role of auxin in activating such kinase activities in cultured cells. Plant J 5: 111-122.

Parker JE, Coleman MJ, Szabo V, Frost LN, Schmidt R, van der Biezen EA, Moores T, Dean C, Daniels MJ, Jones JD (1997) The *Arabidopsis* downy mildew resistance gene RPP5 shares similarity to the toll and interleukin-1 receptors with N and L6. Plant Cell 9: 879-894.

Pines J (1995) Cyclins and cyclin-dependent kinases: a biochemical view. Biochem J 308: 697-711.

Renaudin J—P, Doonan JH, Freeman D, Hashimoto J, Hirt H, Inzé D, Jacobs T, Kouchi H, Rouzé P, Sauter M, Savouré A, Sorrell DA, Sundaresan V, Murray JAH (1996) Plant Cyclins: a unified nomenclature for plant A—, B- and D-type cyclins based on sequence organization. Plant Mol Biol 32: 1003-1018.

Sauter M, Mekhedov SL, Kende H (1995) Gibberellin promotes histone H1 kinase activity and the expression of cdc2 and cyclin genes during the induction of rapid growth in deepwater rice internodes. Plant J 7: 623-632.

Segers G, Gadisseur I, Bergounioux C, de Almeida Engler J, Jacqmard A, Van Montagu M, Inzé D (1996) The Arabidopsis cyclin-dependent kinase gene cdc2bAt is preferentially expressed during S and $G_2$ phases of the cell cycle. Plant J 10: 601-612.

Sherr CJ, Roberts JM (1995) Inhibitors of mammalian G1 cyclin-dependent kinases. Genes Dev 9: 1149-1163.

Soni R, Carmichael JP, Shah ZH, Murray JAH (1995) A family of cyclin D homologs from plants differentially controlled by growth regulators and containing the conserved retinoblastoma protein interaction motif. Plant Cell 7: 85-103.

Wang H, Datla R, Georges F, Loewen M, Cutler AJ (1995) Promoters from kin1 and cor6.6, two homologous *Arabidopsis thaliana* genes: transcriptional regulation and gene expression induced by low temperature, ABA, osmoticum and dehydration. Plant Mol Biol 28: 605-617.

\* cited by examiner

Characterization of cDNA (Wang et al., 1997) and genomic sequences of *ICK1*.
(A). Genomic organization ICK1. Open bars represent exons and filled bars, introns.
(B). Features of cDNA sequence and deduced amino acid sequence.

```
 61  ACGTATATGCAGCTACGGAGCCGGAGAATTGTTTATGTTAGATCGGAAAAATCAAGCTCT  Ick1.seq
  3  ACGTATATGCAGCTACGGAGCCGGAGAATTGTTTATGTTAGATCGGAAAAATCAAGCTCT  ICK1b.seq
  6  ▓▓▓▓▓▓▓▓▓▓▓▓▓▓▓▓▓▓▓▓▓GA TT TTT▓▓▓TAG▓▓▓▓▓▓▓▓▓▓▓▓▓▓▓▓▓▓▓▓▓▓  ICK1c.seq 121  GTCTCCGTCGTCGGTGATAATGGAGTTTCGTCGTCTTGTAGTGGAAGCAATGAATATAAG  Ick1.seq
 63  GTCTCCGTCGTCGGTGATAATGGAG▓▓▓▓▓▓▓▓▓▓▓▓▓▓▓▓▓▓▓▓▓▓▓▓▓▓▓▓▓▓▓▓▓▓  ICK1b.seq
 18  ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  ICK1c.seq 181  AAGAAAGAATTAATACATCTGGAGGAGGAAGATAAAGATGGTGACACTGAAACGTCGACG  Ick1.seq
 88  ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  ICK1b.seq
 18  ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  ICK1c.seq 241  TATCGACGGGGTACGAAGAGGAAGCTTTTTGAAAATCTGAGAGAGGAGGAGAAAGAAGAA  Ick1.seq
 88  ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓  ICK1b.seq
 18  ▓▓▓▓▓▓▓▓▓▓▓▓GGGTACGAAGAGGAAGCTTTTTGAAAATCTGAGAGAGGAGGAGAAAGAAGAA  ICK1c.seq 301  TTAAGTAAATCCATGGAGAATTATTCATCGGAATTTGAATCGGCGGTTAAAGAATCGTTA  Ick1.seq
 88  ▓▓▓▓▓▓▓▓▓▓▓▓▓▓▓AATTATTCATCGGAATTTGAATCGGCGGTTAAAGAATCGTTA  ICK1b.seq
 70  TTAAGTAAATCCATGGAGAATTATTCATCGGAATTTGAATCGGCGGTTAAAGAATCGTTA  ICK1c.seq 361  GATTGTTGTTGTAGCGGGAGGAAAACGATGGAGGAGACGGTGACGGCGGAGGAGGAGGAG  Ick1.seq
130  GATTGTTGTTGTAGCGGGAGGAAAACGATGGAGGAGACGGTGACGGCGGAGGAGGAGGAG  ICK1b.seq
130  GATTGTTGTTGTAGCGGGAGGAAAACGATGGAGGA▓▓▓▓▓▓▓▓▓▓▓▓▓▓▓GAGGAG  ICK1c.seq 421  AAGGCGAAATTGATGACGGAGATGCCAACGGAATCGGAAATTGAAGATTTTTTTGTGGAA  Ick1.seq
190  AAGGCGAAATTGATGACGGAGATGCCAACGGAATCGGAAATTGAAGATTTTTTTGTGGAA  ICK1b.seq
172  AAGGCGAAATTGATGACGGAGATGCCAACGGAATCGGAAATTGAAGATTTTTTTGTGGAA  ICK1c.seq 481  GCTGAGAAACAACTCAAAGAAAAATTCAAGAAGAAGTACAATTTCGATTTCGAGAAGGAG  Ick1.seq
250  GCTGAGAAACAACTCAAAGAAAAATTCAAGAAGAAGTACAATTTCGATTTCGAGAAGGAG  ICK1b.seq
232  GCTGAGAAACAACTCAAAGAAAAATTCAAGAAGAAGTACAATTTCGATTTCGAGAAGGAG  ICK1c.seq 541  AAGCCATTAGAAGGACGTTACGAATGGGTAAAGTTAGAGTGAAGAAGAAGAAGAAGTTTA  Ick1.seq
310  AAGCCATTAGAAGGACGTTACGAATGGGTAAAGTTAGAGTGAAGAAGAAGAAGAAGTTTA  ICK1b.seq
292  AAGCCATTAGAAGGACGTTACGAATGGGTAAAGTTAGAGTGAAGAAGAAGAAGAAGTTTA  ICK1c.seq 601  TGGTTTTTTTTTAACTTTTTAGATTTTAATATTTCAGGGAATAAGTTAATTTTATTTTG  Ick1.seq
370  TGGTTTTTTTTTAACTTTTTAGATTTTAATATTTCAGGGAATAAGTTAATTTTATTTTG  ICK1b.seq
352  TGGTTTTTTTTTAACTTTTTAGATTTT                                   ICK1c.seq 661  TTGATTTGGAAATATAAGATTTGTAGGAGGAATGTTTTTAGAAGTACGAAATTGCACAGA  Ick1.seq
430  TTGATTTGGAAATATA                                              ICK1b.seq
379                                                               ICK1c.seq
```

Alignment of *ICK1* cDNA sequence with *ICK1b* and *ICK1c* showing the differences

Figure 2

```
GTGGAATCTAGGATAATTCTGTCTCCGTGTGTACAGGCGACGAATCGCGGTGGAATTGTG
GCGAGAAATTCAGCAGGAGCGTCGGAGACGAGTGTTGTTATAGTACGACGGCGAGATTCT
CCTCCGGTTGAAGAACAGTGTCAAATCGAAGAAGAAGATTCGTCGGTTTCGTGTTGTTCT
ACATCGGAAGAGAAATCGAAACGGAGAATCGAATTTGTAGATCTTGAGGAAAATAACGGT
GACGATCGTGAAACAGAAACGTCGTGGATTTACGATGATTTGAATAAGAGTGAGGAATCG
ATGAACATGGATTCTTCTTCGGTGGCTGTTGAAGATGTAGAGTCTCGCCGCAGGTTAAGG
AAGAGTCTCCATGAGACGGTGAAGGAAGCTGAGTTAGAAGACTTTTTTCAGGTGGCGGAG
AAAGATCTTCGGAATAAGTTGTTGGAATGTTCTATGAAGTATAACTTCGATTTCGAGAAA
GATGAGCCACTTGGTGGAGGAAGATACGAGTGGGTTAAATTGAATCCATGAAGAAGACGA
TGATGATAATGATGATCATTGTTTTCACCAAAGTACTTATTATTTCTCTTCTGTAATAAT
CTTTGCTTTGATTTTTCTTTTAACAAAATCCAAATGTAGATATCTTTCTCTCGAATAATC
AATAACATGTAATTCAACTTTTGTTTGTACTTCCTTGAGGTAATTAATTAGATTCGTGTT
TTTCTCGATTAATAAACTATAAGTTTATAACTAAA
```

**cDNA sequence of *ICK2***

Figure 3

```
AAAAAAAAGCAGAGAGAGAGAGCACACAAAAATCCAAGAGAGAAAAAAATGAGCGAGAGA
AAGCGAGAGCTTGCAGAAGAAGCTTCAAGCACAAGCTTCTCACCACTGAAGAAAACGAAG
CTTAATGATTCTTCTGATTCATCACCGGACTCTCATGACGTCATCGTCTTCGCGGTTTCA
TCTTCTTCCGTTGCTTCGTCGGCGGCTTTAGCGTCTGATGAATGTTCCGTTACCATCGGT
GGAGAAGAAAGTGATCAGTCCTCGAGTATCAGCTCCGGTTGTTTCACCAGTGAATCGAAA
GAAATCGCGAAGAACAGTTCGTCGTTTGGTGTAGATCTGGAGGATCATCAAATCGAAACC
GAAACCGAAACCTCAACATTCATCACCAGCAATTTCAGAAAAGAGACGAGTCCAGTGAGT
GAGGGTTTGGGAGAAACGACAACAGAAATGGAATCATCATCGGCAACGAAGAGAAAACAA
CCGGGGGTGAGGAAGACTCCAACGGCGGCGGAGATTGAGGATTTGTTCTCGGAGCTAGAG
AGTCAAGACGATAAGAAGAAGCAATTCATAGAAAAGTACAACTTCGATATTGTCAATGAC
GAACCGCTTGAAGGTCGCTACAAGTGGGATCGACTTTAAGCCATCAAAAAGCAAATACCA
TCCATGAAGAAGACAAAAGAAAAATAGGTTTTGTTTTTCGTGGTTAACATTTCCACTTGT
ACAGCTCTAGTCTATTTCTCTTTAAAAACCTATGTTACTAGTTCGTACAAAACAAAACAA
AAAACACGACCTTTATAATGAAATTTCGGATCTTGGCTACTAAA
```

**cDNA sequence of *ICN2***

Figure 4

```
CTCTCTCCAGAGAAAACTATAATGAGCTTGAGAGAAATGAGCGAAACAAAACCCAAGAGA
GATTCTGAGTACGAAGGATCAAACATCAAGAGGATGAGACTCGATGATGATGATGACGTT
TTACGCTCACCGACGAGAACTCTTTCTTCTTCTTCCTCTTCTTCTCTGGCTTACTCGGTT
TCAGATTCCGGAGGTTTCTGCTCCGTCGCGTTATCTGAAGAAGAAGACGATCATCTAAGC
TCAAGCATCAGCTCTGGTTGTTCCAGCAGCGAAACTAACGAAATCGCTACTCGTCTTCCA
TTTTCAGATCTGGAGGCTCATGAAATCTCCGAAACCGAAATCTCAACGTTACTCACCAAC
AATTTCAGGAAACAGGGAATTTCATCAAGCGAGAATCTGGGAGAAACAGCAGAAATGGAC
TCGGCGACGACGGAGATGAGAGATCAGAGAAAGACGGAGAAGAAGAAGAAGATGGAAAAA
TCACCGACGCAGGCAGAGCTTGATGACTTTTTCTCGGCGGCGGAGAGATACGAACAGAAA
CGATTCACAGAAAAGTACAACTACGACATCGTCAATGATACGCCGCTTGAAGGTCGGTAC
CAGTGGGTTAGTCTGAAACCTTAGAAGCCATGGAAGAACAAA
```

**cDNA sequence of *ICN6***

Figure 5

```
ATTAAAGAGTCTGGTTCCAGGTCTCGCGTTGACTCGGTTAACTCGGCTCCTGTAGCTCAG
AGCTCTAATGAAGATGAATGTTTTGACAATTTCGTGAGTGTCCAAGTTTCTTGTGGTGAA
AACAGTCTCGGTTTTGAATCAAGACACAGCACAAGGGAGAGCACGCCTTGTAACTTTGTT
GAGGATATGGAGATCATGGTTACACCAGGGTCTAGCACGAGGTCGATGTGCAGAGCAACC
AAAGAGTACACAAGGGAACAAGATAACGTGATCCCGACCACTAGTGAAATGGAGGAGTTC
TTTGCATATGCAGAGCAGCAGCAACAGAGGCTATTCATGGAGAAGTACAACTTCGACATT
GTGAATGATATCCCCCTCAGCGGACGTTACGAATGGGTGCAAGTCAAACCATGAAGTTCA
AAAGGAAACAGCTCCAAAAGACATGGTGTGAAGTTAGAGAATTGTGATGGAGTTTAACAG
AACTAACCAAACATCAGAAATCGTGTTAATCCTTAAGTTAATAATGTGGGTTA
``` cDNA sequence of *ICN7*

SEQ ID NO. 15: The nucleotide sequence of *Chenopodium rubrum* CDKI1 (GenBank AJ002173)

gcacgagcgaaattgcggtggtaggagttaaaaccagagctcgagactgccctagctatggcggcagctgctactccaac
ttcgtctccggcgaagaagatcaagaaggtttcgaagtcgtcgtataatattcctcaactaagaagtcgtcgaaagaatt
tgtcggcgccggagaatttcgccgaattagaaacgacgccgttggaagttgcggcggttgttgaggaggaagaggttgcg
aattgctcgagtagcgaggtaattactacagctaggtcggattttccgccgtcttgttgctcaagcaattatgatcagtt
gagttctagcgagccagaagtagttaaggatgatgatggtttgggaaatcgtacagcagatccagaggttgagagtggtg
aggcgtcgtcaaagcaaaaggagagccatagaacagaagcgagagaagctacaaaattagacgaccaggattatccggcg
acgaaatcaacggtacagatcaagatgccgtctgattcagaaatcgaagaattctttgctgttgctgaaaaagatctcca
gaaacgcttcagcgaaaagtacaatttcgacatagttaaggacgtgccactgaaaggtcgttatgattgggttccaataa
atccatgaataaaacccactggtgatagtgatgatgatgaatgactgaattcttccacaattacgccaaaattagccact
gaaattgcaaagtaaatctttaattttagccttttctttcttttagcagaagttgatctattctcacaccgaaaaaaaa
aaaa

SEQ ID NO. 16: The amino acid sequence of *Chenopodium rubrum* CDKI1

MAAAATPTSS PAKKIKKVSK SSYNIPQLRS RRKNLSAPEN FAELETTPLE
VAAVVEEEEVANCSSSEVIT TARSDFPPSC CSSNYDQLSS SEPEVVKDDD
GLGNRTADPE VESGEASSKQ KESHRTEARE ATKLDDQDYP ATKSTVQIKM
PSDSEIEEFF AVAEKDLQKR FSEKYNFDIV KDVPLKGRYD WVPINP

Figure 6

```
                                                                                         Consensus
    .........................................................................S......... . Consensus
  1 MVRKYRKA-----------------KGIVEAGVSSTYMQLRSRRIV----YVRSEKSSS SVVGDNG SS  C GSNEYKKELIHL  EEDKDGD  ICK1.pro
  1 V-------ESRIILSPCVQATNRGGIVARN AGA---------------SETSV IVRRRD PPV-----EEQ ---QI  EEDS V ------  ICK2.pro
  1 KKKQRERAHKNPREKKMSERKRELAEEA STSFSPLKKTKLNDSDSSPDSHDVI FAV SSS AS AALASDE SVTIGGE SDQ- SS ------  ICN2.pro
  1 LS--PEKTIMSLREMSETKPKRDSEYEG N------IKRMRLDDDDDVLRSPTRTLS-SS SSS LAY EV DSGGF SVALSEE DDHL S ----  ICN6.pro
  1 IKESGSRSRVD---------------------------------------------- VN PVAQ SNEDE  FDNFV-------------  ICN7.pro ...C..SE.K--........F..DLE......E................F.K...E.L.E.......S......R.......K.K.....PT.AE.E  Consensus
 74 TETSTYRRGT          ----RKLCEN REEEKEELSKSMENYSSE    ---ESAVK  S DCCCSGRKTMEETV-TAEEEE A LMTEMP ES   I  ICK1.pro
 58 ---C ST  E  ----SKRRIE -V         ENNGDDRETETSWIYDDLN SEESM--NMDSSSVAVEDVESRR    ----LR  SLHETVKE L  L   ICK2.pro
 90 ISSG FTS S EIAKNSSS GV    DHQIET  TETSTFITSN  ETSPVS G TTTEME SSATK    ---QPGVRKT  A GI    ICN2.pro
 83 ISSG SS  TNEIATRLP- S--  AHEI-S  TEISTLLTNN R QGISSS N GTA-EMD ATTEM DQRKTE K MEKS  QA LD   ICN6.pro
 34 VQVS GEN-------SLGF SRHSTR STPCNFV------ DM- IMVTPG STRSMCRATKEYTREQDNVI  TS M    ICN7.pro DFF..AE...Q.....F.E---KYNFDIVND.PLEG-RYEWV.L.P-                                        Consensus
154  VE  K---- LKEK KK--- FEKEK       KLE .                                              ICK1.pro
134  QV  K--DLRNKLL CSM            FEKE   G        K N  .                                 ICK2.pro
174 L SEL SQDDKKKQ                    K   ----DRL                                       ICN2.pro
169 SA RYE KR--T         Y      -  Q SK  .                                               ICN6.pro
 99 E AY   --Q QQRL M              I S      QVK                                           ICN7.pro Consensus 'Consensus #1': When 60% (3) match the residue of the Consensus show the residue of the
Consensus, otherwise show '.'.

Decoration 'Decoration #1': Shade (with black at 40% fill) residues that match the consensus named
'Consensus #1' exactly.
```

**Alignment of deduced amino acid sequences of *ICK1, ICK2, ICN2, ICN6 and ICN7***

Figure 7

| Bait | ICK1 (Numbers indicate the amino acid positions) | Filter assay | Activity |
|---|---|---|---|
| cdc2a | / | | 0.0 |
| / | (3-191) | | 0.0 |
| cdc2a | (3-191) | | 12.4 |
| cdc2a | (73-191) | | 40.6 |
| cdc2a | (109-191) | | 42.6 |
| cdc2a | (154-191) | | 10.7 |
| cdc2a | (3-175) | | 0.3 |
| cdc2a | (3-162) | | 0.3 |
| cdc2a | (3-152) | | 0.0 |
| cyclin δ3 | / | | 0.8 |
| cyclin δ3 | (3-191) | | 100.0 |
| cyclin δ3 | (73-191) | | 397.3 |
| cyclin δ3 | (109-191) | | 480.7 |
| cyclin δ3 | (154-191) | | 7.1 |
| cyclin δ3 | (3-175) | | 19.9 |
| cyclin δ3 | (3-162) | | 2.5 |
| cyclin δ3 | (3-152) | | 2.2 |
| ATMPK2 | (3-191) | | 0.0 |

Figure 8

SEQUENCE LISTING

```
<160> NUMBER OF SEQ ID NOS:  16

<210> SEQ ID NO 1
<211> LENGTH: 904
<212> TYPE: DNA
<213> ORGANISM: Arabidopsis thaliana
<220> FEATURE:
<221> NAME/KEY: CDS
<222> LOCATION: (55)..(627)
<221> NAME/KEY: intron
<222> LOCATION: (252)..(253)
<221> NAME/KEY: intron
<222> LOCATION: (296)..(297)
<221> NAME/KEY: intron
<222> LOCATION: (563)..(564)

<400> SEQUENCE: 1
atctctctct ctcacagaga ttgtaacttc acgcacacgt aacctaaatc gaag atg        57
                                                            Met
                                                            1 gtg aga aaa tat aga aaa gct aaa gga att gta gaa gct gga gtt tcg      105
Val Arg Lys Tyr Arg Lys Ala Lys Gly Ile Val Glu Ala Gly Val Ser
        5                  10                  15 tca acg tat atg cag cta cgg agc cgg aga att gtt tat gtt aga tcg      153
Ser Thr Tyr Met Gln Leu Arg Ser Arg Arg Ile Val Tyr Val Arg Ser
     20                  25                  30 gaa aaa tca agc tct gtc tcc gtc gtc ggt gat aat gga gtt tcg tcg      201
Glu Lys Ser Ser Ser Val Ser Val Val Gly Asp Asn Gly Val Ser Ser
 35                  40                  45 tct tgt agt gga agc aat gaa tat aag aag aaa gaa tta ata cat ctg      249
Ser Cys Ser Gly Ser Asn Glu Tyr Lys Lys Lys Glu Leu Ile His Leu
 50                  55                  60                  65 gag gag gaa gat aaa gat ggt gac act gaa acg tcg acg tat cga cgg      297
Glu Glu Glu Asp Lys Asp Gly Asp Thr Glu Thr Ser Thr Tyr Arg Arg
                 70                  75                  80 gtg acg aag agg aag ctt ttt gaa aat ctg aga gag gag gag aaa gaa      345
Val Thr Lys Arg Lys Leu Phe Glu Asn Leu Arg Glu Glu Glu Lys Glu
             85                  90                  95
```

-continued

```
gaa tta agt aaa tcc atg gag aat tat tca tcg gaa ttt gaa tcg gcg      393
Glu Leu Ser Lys Ser Met Glu Asn Tyr Ser Ser Glu Phe Glu Ser Ala
            100                 105                 110 gtt aaa gaa tcg tta gat tgt tgt tgt agc ggg agg aaa acg atg gag      441
Val Lys Glu Ser Leu Asp Cys Cys Cys Ser Gly Arg Lys Thr Met Glu
    115                 120                 125 gag acg gtg acg gcg gag gag gag gag aag gcg aaa ttg atg acg gag      489
Glu Thr Val Thr Ala Glu Glu Glu Glu Lys Ala Lys Leu Met Thr Glu
130                 135                 140                 145 atg cca acg gaa tcg gaa att gaa gat ttt ttt gtg gaa gct gag aaa      537
Met Pro Thr Glu Ser Glu Ile Glu Asp Phe Phe Val Glu Ala Glu Lys
                150                 155                 160 caa ctc aaa gaa aaa ttc aag aag aag tac aat ttc gat ttc gag aag      585
Gln Leu Lys Glu Lys Phe Lys Lys Lys Tyr Asn Phe Asp Phe Glu Lys
            165                 170                 175 gag aag cca tta gaa gga cgt tac gaa tgg gta aag tta gag              627
Glu Lys Pro Leu Glu Gly Arg Tyr Glu Trp Val Lys Leu Glu
        180                 185                 190 tgaagaagaa gaagaagttt atggttttt ttttaacttt ttagattta atatttcagg      687 gaataagtta attttatttt gttgatttgg aaatataaga tttgtaggag gaatgttttt    747
agaagtacga aattgcacag aaaaagaaga aagcttttta acagatttta gagcccagaa    807
aagtcgtgtc ttttagctct acttttacct cttcttcgaa tcttgtgtat cttttagcat    867
attctttagt acatttttat gtttttggtg actgata                             904

<210> SEQ ID NO 2
<211> LENGTH: 191
<212> TYPE: PRT
<213> ORGANISM: Arabidopsis thaliana

<400> SEQUENCE: 2

Met Val Arg Lys Tyr Arg Lys Ala Lys Gly Ile Val Glu Ala Gly Val
1               5                   10                  15

Ser Ser Thr Tyr Met Gln Leu Arg Ser Arg Arg Ile Val Tyr Val Arg
            20                  25                  30

Ser Glu Lys Ser Ser Ser Val Ser Val Val Gly Asp Asn Gly Val Ser
        35                  40                  45

Ser Ser Cys Ser Gly Ser Asn Glu Tyr Lys Lys Glu Leu Ile His
    50                  55                  60

Leu Glu Glu Glu Asp Lys Asp Gly Asp Thr Glu Thr Ser Thr Tyr Arg
65                  70                  75                  80

Arg Val Thr Lys Arg Lys Leu Phe Glu Asn Leu Arg Glu Glu Lys
                85                  90                  95

Glu Glu Leu Ser Lys Ser Met Glu Asn Tyr Ser Ser Glu Phe Glu Ser
            100                 105                 110

Ala Val Lys Glu Ser Leu Asp Cys Cys Cys Ser Gly Arg Lys Thr Met
        115                 120                 125

Glu Glu Thr Val Thr Ala Glu Glu Glu Glu Lys Ala Lys Leu Met Thr
    130                 135                 140

Glu Met Pro Thr Glu Ser Glu Ile Glu Asp Phe Phe Val Glu Ala Glu
145                 150                 155                 160

Lys Gln Leu Lys Glu Lys Phe Lys Lys Lys Tyr Asn Phe Asp Phe Glu
                165                 170                 175

Lys Glu Lys Pro Leu Glu Gly Arg Tyr Glu Trp Val Lys Leu Glu
            180                 185                 190
```

-continued

<210> SEQ ID NO 3
<211> LENGTH: 660
<212> TYPE: DNA
<213> ORGANISM: Arabidopsis thaliana

<400> SEQUENCE: 3

| | | | | | |
|---|---|---|---|---|---|
| acgtatatgc | agctacggag | ccggagaatt | gtttatgtta | gatcggaaaa | atcaagctct | 60 |
| gtctccgtcg | tcggtgataa | tggagtttcg | tcgtcttgta | gtggaagcaa | tgaatataag | 120 |
| aagaaagaat | taatacatct | ggaggaggaa | gataaagatg | gtgacactga | aacgtcgacg | 180 |
| tatcgacggg | gtacgaagag | gaagcttttt | gaaaatctga | gagaggagga | gaaagaagaa | 240 |
| ttaagtaaat | ccatggagaa | ttattcatcg | gaatttgaat | cggcggttaa | agaatcgtta | 300 |
| gattgttgtt | gtagcgggag | gaaaacgatg | gaggagacgg | tgacggcgga | ggaggaggag | 360 |
| aaggcgaaat | tgatgacgga | gatgccaacg | gaatcggaaa | ttgaagattt | ttttgtggaa | 420 |
| gctgagaaac | aactcaaaga | aaaattcaag | aagaagtaca | atttcgattt | cgagaaggag | 480 |
| aagccattag | aaggacgtta | cgaatgggta | aagttagagt | gaagaagaag | aagaagttta | 540 |
| tggttttttt | tttaactttt | tagattttaa | tatttcaggg | aataagttaa | ttttatttg | 600 |
| ttgatttgga | aatataagat | ttgtaggagg | aatgttttta | gaagtacgaa | attgcacaga | 660 |

<210> SEQ ID NO 4
<211> LENGTH: 443
<212> TYPE: DNA
<213> ORGANISM: Arabidopsis thaliana

<400> SEQUENCE: 4

| | | | | | |
|---|---|---|---|---|---|
| acgtatatgc | agctacggag | ccggagaatt | gtttatgtta | gatcggaaaa | atcaagctct | 60 |
| gtctccgtcg | tcggtgataa | tggagaatta | ttcatcggaa | tttgaatcgg | cggttaaaga | 120 |
| atcgttagat | tgttgttgta | gcgggaggaa | aacgatggag | gagacggtga | cggcggagga | 180 |
| ggaggagaag | gcgaaattga | tgacggagat | gccaacggaa | tcggaaattg | aagatttttt | 240 |
| tgtggaagct | gagaaacaac | tcaaagaaaa | attcaagaag | aagtacaatt | tcgatttcga | 300 |
| gaaggagaag | ccattagaag | gacgttacga | atgggtaaag | ttagagtgaa | gaagaagaag | 360 |
| aagtttatgg | tttttttttt | aacttttttag | attttaatat | ttcagggaat | aagttaattt | 420 |
| tattttgttg | atttggaaat | ata | | | | 443 |

<210> SEQ ID NO 5
<211> LENGTH: 377
<212> TYPE: DNA
<213> ORGANISM: Arabidopsis thaliana

<400> SEQUENCE: 5

| | | | | | |
|---|---|---|---|---|---|
| gagttatttt | aggggtacga | agaggaagct | ttttgaaaat | ctgagagagg | aggagaaaga | 60 |
| agaattaagt | aaatccatgg | agaattattc | atcggaattt | gaatcggcgg | ttaaagaatc | 120 |
| gttagattgt | tgttgtagcg | ggaggaaaac | gatggaggag | gaggaggaga | aggcgaaatt | 180 |
| gatgacggag | atgccaacgg | aatcggaaat | tgaagatttt | tttgtggaag | ctgagaaaca | 240 |
| actcaaagaa | aaattcaaga | agaagtacaa | tttcgatttc | gagaaggaga | agccattaga | 300 |
| aggacgttac | gaatgggtaa | agttagagtg | aagaagaaga | agaagtttat | ggttttttttt | 360 |
| ttaactttt | agatttt | | | | | 377 |

<210> SEQ ID NO 6
<211> LENGTH: 755

-continued

```
<212> TYPE: DNA
<213> ORGANISM: Arabidopsis thaliana

<400> SEQUENCE: 6
gtggaatcta ggataattct gtctccgtgt gtacaggcga cgaatcgcgg tggaattgtg      60
gcgagaaatt cagcaggagc gtcggagacg agtgttgtta tagtacgacg gcgagattct     120
cctccggttg aagaacagtg tcaaatcgaa gaagaagatt cgtcggtttc gtgttgttct     180
acatcggaag agaaatcgaa acggagaatc gaatttgtag atcttgagga aaataacggt     240
gacgatcgtg aaacagaaac gtcgtggatt tacgatgatt tgaataagag tgaggaatcg     300
atgaacatgg attcttcttc ggtggctgtt gaagatgtag agtctcgccg caggttaagg     360
aagagtctcc atgagacggt gaaggaagct gagttagaag acttttttca ggtggcggag     420
aaagatcttc ggaataagtt gttggaatgt tctatgaagt ataacttcga tttcgagaaa     480
gatgagccac ttggtggagg aagatacgag tgggttaaat tgaatccatg aagaagacga     540
tgatgataat gatgatcatt gttttcacca agtacttat tatttctctt ctgtaataat      600
ctttgctttg atttttcttt taacaaaatc caaatgtaga tatctttctc tcgaataatc     660
aataacatgt aattcaactt ttgtttgtac ttccttgagg taattaatta gattcgtgtt     720
tttctcgatt aataaactat aagtttataa ctaaa                                755

<210> SEQ ID NO 7
<211> LENGTH: 824
<212> TYPE: DNA
<213> ORGANISM: Arabidopsis thaliana

<400> SEQUENCE: 7
aaaaaaaagc agagagagag agcacacaaa atccaagag agaaaaaaat gagcgagaga       60
aagcgagagc ttgcagaaga agcttcaagc acaagcttct caccactgaa gaaaacgaag     120
cttaatgatt cttctgattc atcaccggac tctcatgacg tcatcgtctt cgcggtttca     180
tcttcttccg ttgcttcgtc ggcggcttta gcgtctgatg aatgttccgt taccatcggt     240
ggagaagaaa gtgatcagtc ctcgagtatc agctccggtt gtttcaccag tgaatcgaaa     300
gaaatcgcga agaacagttc gtcgtttggt gtagatctgg aggatcatca aatcgaaacc     360
gaaaccgaaa cctcaacatt catcaccagc aatttcagaa aagagacgag tccagtgagt     420
gagggtttgg gagaaacgac aacagaaatg gaatcatcat cggcaacgaa gagaaaacaa     480
ccggggtga ggaagactcc aacggcggcg gagattgagg atttgttctc ggagctagag      540
agtcaagacg ataagaagaa gcaattcata gaaagtaca acttcgatat tgtcaatgac      600
gaaccgcttg aaggtcgcta caagtgggat cgactttaag ccatcaaaaa gcaaatacca    660
tccatgaaga agacaaaaga aaaataggtt ttgttttcg tggttaacat ttccacttgt     720
acagctctag tctatttctc tttaaaaacc tatgttacta gttcgtacaa acaaaaacaa    780
aaaacacgac ctttataatg aaattcggga tcttggctac taaa                     824

<210> SEQ ID NO 8
<211> LENGTH: 642
<212> TYPE: DNA
<213> ORGANISM: Arabidopsis thaliana

<400> SEQUENCE: 8
ctctctccag agaaaactat aatgagcttg agagaaatga gcgaaacaaa acccaagaga      60
gattctgagt acgaaggatc aaacatcaag aggatgagac tcgatgatga tgatgacgtt    120
```

```
ttacgctcac cgacgagaac tctttcttct tcttcctctt cttctctggc ttactcggtt      180
tcagattccg gaggtttctg ctccgtcgcg ttatctgaag aagaagacga tcatctaagc      240
tcaagcatca gctctggttg ttccagcagc gaaactaacg aaatcgctac tcgtcttcca      300
ttttcagatc tggaggctca tgaaatctcc gaaaccgaaa tctcaacgtt actcaccaac      360
aatttcagga acagggaat ttcatcaagc gagaatctgg gagaaacagc agaaatggac       420
tcggcgacga cggagatgag agatcagaga agacggaga agaagaagaa gatggaaaaa       480
tcaccgacgc aggcagagct tgatgacttt ttctcggcgg cggagagata cgaacagaaa      540
cgattcacag aaaagtacaa ctacgacatc gtcaatgata cgccgcttga aggtcggtac      600
cagtgggtta gtctgaaacc ttagaagcca tggaagaaca aa                         642

<210> SEQ ID NO 9
<211> LENGTH: 533
<212> TYPE: DNA
<213> ORGANISM: Arabidopsis thaliana

<400> SEQUENCE: 9
attaaagagt ctggttccag gtctcgcgtt gactcggtta actcggctcc tgtagctcag       60
agctctaatg aagatgaatg ttttgacaat tcgtgagtg tccaagtttc ttgtggtgaa       120
aacagtctcg gttttgaatc aagacacagc acaagggaga gcacgccttg taactttgtt      180
gaggatatgg agatcatggt tacaccaggg tctagcacga ggtcgatgtg cagagcaacc      240
aaagagtaca aagggaaca agataacgtg atcccgacca ctagtgaaat ggaggagttc       300
tttgcatatg cagagcagca gcaacagagg ctattcatgg agaagtacaa cttcgacatt      360
gtgaatgata tccccctcag cggacgttac gaatgggtgc aagtcaaacc atgaagttca      420
aaaggaaaca gctccaaaag acatggtgtg aagttagaga attgtgatgg agtttaacag      480
aactaaccaa acatcagaaa tcgtgttaat ccttaagtta ataatgtggg tta             533

<210> SEQ ID NO 10
<211> LENGTH: 191
<212> TYPE: PRT
<213> ORGANISM: Arabidopsis thaliana

<400> SEQUENCE: 10

Met Val Arg Lys Tyr Arg Lys Ala Lys Gly Ile Val Glu Ala Gly Val
  1               5                  10                  15

Ser Ser Thr Tyr Met Gln Leu Arg Ser Arg Arg Ile Val Tyr Val Arg
             20                  25                  30

Ser Glu Lys Ser Ser Ser Val Ser Val Val Gly Asp Asn Gly Val Ser
         35                  40                  45

Ser Ser Cys Ser Gly Ser Asn Glu Tyr Lys Lys Lys Glu Leu Ile His
     50                  55                  60

Leu Glu Glu Glu Asp Lys Asp Gly Asp Thr Glu Thr Ser Thr Tyr Arg
 65                  70                  75                  80

Arg Gly Thr Lys Arg Lys Leu Cys Glu Asn Leu Arg Glu Glu Lys
                 85                  90                  95

Glu Glu Leu Ser Lys Ser Met Glu Asn Tyr Ser Ser Glu Phe Glu Ser
            100                 105                 110

Ala Val Lys Glu Ser Leu Asp Cys Cys Cys Ser Gly Arg Lys Thr Met
            115                 120                 125

Glu Glu Thr Val Thr Ala Glu Glu Glu Lys Ala Lys Leu Met Thr
            130                 135                 140
```

```
Glu Met Pro Thr Glu Ser Glu Ile Glu Asp Phe Phe Val Glu Ala Glu
145                 150                 155                 160

Lys Gln Leu Lys Glu Lys Phe Lys Lys Lys Tyr Asn Phe Asp Phe Glu
                165                 170                 175

Lys Glu Lys Pro Leu Gly Gly Arg Tyr Glu Trp Val Lys Leu Glu
            180                 185                 190

<210> SEQ ID NO 11
<211> LENGTH: 176
<212> TYPE: PRT
<213> ORGANISM: Arabidopsis thaliana

<400> SEQUENCE: 11

Val Glu Ser Arg Ile Ile Leu Ser Pro Cys Val Gln Ala Thr Asn Arg
1               5                   10                  15

Gly Gly Ile Val Ala Arg Asn Ser Ala Gly Ser Glu Thr Ser Val
            20                  25                  30

Val Ile Val Arg Arg Asp Ser Pro Val Glu Glu Gln Cys Gln
        35                  40                  45

Ile Glu Glu Asp Ser Ser Val Ser Cys Cys Ser Thr Ser Glu Glu
    50                  55                  60

Lys Ser Lys Arg Arg Ile Glu Phe Val Asp Leu Glu Glu Asn Asn Gly
65                  70                  75                  80

Asp Asp Arg Glu Thr Glu Thr Ser Trp Ile Tyr Asp Leu Asn Lys
                85                  90                  95

Ser Glu Glu Ser Met Asn Met Asp Ser Ser Val Ala Val Glu Asp
                100                 105                 110

Val Glu Ser Arg Arg Arg Leu Arg Lys Ser Leu His Glu Thr Val Lys
            115                 120                 125

Glu Ala Glu Leu Glu Asp Phe Phe Gln Val Ala Glu Lys Asp Leu Arg
130                 135                 140

Asn Lys Leu Leu Glu Cys Ser Met Lys Tyr Asn Phe Asp Phe Glu Lys
145                 150                 155                 160

Asp Glu Pro Leu Gly Gly Gly Arg Tyr Glu Trp Val Lys Leu Asn Pro
                165                 170                 175

<210> SEQ ID NO 12
<211> LENGTH: 212
<212> TYPE: PRT
<213> ORGANISM: Arabidopsis thaliana

<400> SEQUENCE: 12

Lys Lys Lys Gln Arg Glu Arg Ala His Lys Asn Pro Arg Glu Lys Lys
1               5                   10                  15

Met Ser Glu Arg Lys Arg Glu Leu Ala Glu Ala Ser Ser Thr Ser
            20                  25                  30

Phe Ser Pro Leu Lys Lys Thr Lys Leu Asn Asp Ser Ser Asp Ser Ser
        35                  40                  45

Pro Asp Ser His Asp Val Ile Val Phe Ala Val Ser Ser Ser Val
    50                  55                  60

Ala Ser Ser Ala Ala Leu Ala Ser Asp Glu Cys Ser Val Thr Ile Gly
65                  70                  75                  80

Gly Glu Glu Ser Asp Gln Ser Ser Ser Ile Ser Ser Gly Cys Phe Thr
                85                  90                  95

Ser Glu Ser Lys Glu Ile Ala Lys Asn Ser Ser Ser Phe Gly Val Asp
                100                 105                 110
```

-continued

```
Leu Glu Asp His Gln Ile Glu Thr Glu Thr Ser Thr Phe Ile
        115                 120                 125

Thr Ser Asn Phe Arg Lys Glu Thr Ser Pro Val Ser Glu Gly Leu Gly
130                 135                 140

Glu Thr Thr Thr Glu Met Glu Ser Ser Ser Ala Thr Lys Arg Lys Gln
145                 150                 155                 160

Pro Gly Val Arg Lys Thr Pro Thr Ala Ala Glu Ile Glu Asp Leu Phe
                165                 170                 175

Ser Glu Leu Glu Ser Gln Asp Lys Lys Lys Gln Phe Ile Glu Lys
            180                 185                 190

Tyr Asn Phe Asp Ile Val Asn Asp Glu Pro Leu Glu Gly Arg Tyr Lys
                195                 200                 205

Trp Asp Arg Leu
    210
```

<210> SEQ ID NO 13
<211> LENGTH: 208
<212> TYPE: PRT
<213> ORGANISM: Arabidopsis thaliana

<400> SEQUENCE: 13

```
Leu Ser Pro Glu Lys Thr Ile Met Ser Leu Arg Glu Met Ser Glu Thr
1               5                   10                  15

Lys Pro Lys Arg Asp Ser Glu Tyr Glu Gly Ser Asn Ile Lys Arg Met
                20                  25                  30

Arg Leu Asp Asp Asp Asp Val Leu Arg Ser Pro Thr Arg Thr Leu
            35                  40                  45

Ser Ser Ser Ser Ser Ser Leu Ala Tyr Ser Val Ser Asp Ser Gly
        50                  55                  60

Gly Phe Cys Ser Val Ala Leu Ser Glu Glu Glu Asp Asp His Leu Ser
65                  70                  75                  80

Ser Ser Ile Ser Ser Gly Cys Ser Ser Ser Glu Thr Asn Glu Ile Ala
                85                  90                  95

Thr Arg Leu Pro Phe Ser Asp Leu Glu Ala His Glu Ile Ser Glu Thr
                100                 105                 110

Glu Ile Ser Thr Leu Leu Thr Asn Asn Phe Arg Lys Gln Gly Ile Ser
            115                 120                 125

Ser Ser Glu Asn Leu Gly Glu Thr Ala Glu Met Asp Ser Ala Thr Thr
130                 135                 140

Glu Met Arg Asp Gln Arg Lys Thr Glu Lys Lys Lys Met Glu Lys
145                 150                 155                 160

Ser Pro Thr Gln Ala Glu Leu Asp Asp Asp Phe Phe Ser Ala Ala Glu
                165                 170                 175

Arg Tyr Glu Gln Lys Arg Phe Thr Glu Lys Tyr Asn Tyr Asp Ile Val
            180                 185                 190

Asn Asp Thr Pro Leu Glu Gly Arg Tyr Gln Trp Val Ser Leu Lys Pro
                195                 200                 205
```

<210> SEQ ID NO 14
<211> LENGTH: 137
<212> TYPE: PRT
<213> ORGANISM: Arabidopsis thaliana

<400> SEQUENCE: 14

```
Ile Lys Glu Ser Gly Ser Arg Ser Arg Val Asp Ser Val Asn Ser Val
1               5                   10                  15
```

-continued

```
Pro Val Ala Gln Ser Ser Asn Glu Asp Glu Cys Phe Asp Asn Phe Val
             20                  25                  30
Ser Val Gln Val Ser Cys Gly Glu Asn Ser Leu Gly Phe Glu Ser Arg
         35                  40                  45
His Ser Thr Arg Glu Ser Thr Pro Cys Asn Phe Val Glu Asp Met Glu
     50                  55                  60
Ile Met Val Thr Pro Gly Ser Ser Thr Arg Ser Met Cys Arg Ala Thr
 65                  70                  75                  80
Lys Glu Tyr Thr Arg Glu Gln Asp Asn Val Ile Pro Thr Thr Ser Glu
                 85                  90                  95
Met Glu Glu Phe Phe Ala Tyr Ala Glu Gln Gln Gln Arg Leu Phe
             100                 105                 110
Met Glu Lys Tyr Asn Phe Asp Ile Val Asn Asp Ile Pro Leu Ser Gly
         115                 120                 125
Arg Tyr Glu Trp Val Gln Val Lys Pro
     130                 135
```

<210> SEQ ID NO 15
<211> LENGTH: 804
<212> TYPE: DNA
<213> ORGANISM: Chenopodium rubrum

<400> SEQUENCE: 15

```
gcacgagcga aattgcggtg gtaggagtta aaaccagagc tcgagactgc cctagctatg    60
gcggcagctg ctactccaac ttcgtctccg gcgaagaaga tcaagaaggt ttcgaagtcg   120
tcgtataata ttcctcaact aagaagtcgt cgaaagaatt tgtcggcgcc ggagaatttc   180
gccgaattag aaacgacgcc gttggaagtt gcggcggttg ttgaggagga agaggttgcg   240
aattgctcga gtagcgaggt aattactaca gctaggtcgg attttccgcc gtcttgttgc   300
tcaagcaatt atgatcagtt gagttctagc gagccagaag tagttaagga tgatgatggt   360
ttgggaaatc gtacagcaga tccagaggtt gagagtggtg aggcgtcgtc aaagcaaaag   420
gagagccata aacagaagc gagagaagct acaaaattag acgaccagga ttatccggcg   480
acgaaatcaa cggtacagat caagatgccg tctgattcag aaatcgaaga attctttgct   540
gttgctgaaa agatctccag aaacgcttc agcgaaagt acaatttcga catagttaag   600
gacgtgccac tgaaaggtcg ttatgattgg gttccaataa atccatgaat aaaacccact   660
ggtgatagtg atgatgatga atgactgaat tcttccacaa ttacgccaaa attagccact   720
gaaattgcaa agtaaatctt taattttagc cttttctttc tttttagcag aagttgatct   780
attctcacac cgaaaaaaaa aaaa                                           804
```

<210> SEQ ID NO 16
<211> LENGTH: 196
<212> TYPE: PRT
<213> ORGANISM: Chenopodium rubrum

<400> SEQUENCE: 16

```
Met Ala Ala Ala Ala Thr Pro Thr Ser Ser Pro Ala Lys Lys Ile Lys
  1               5                  10                  15
Lys Val Ser Lys Ser Ser Tyr Asn Ile Pro Gln Leu Arg Ser Arg Arg
             20                  25                  30
Lys Asn Leu Ser Ala Pro Glu Asn Phe Ala Glu Leu Glu Thr Thr Pro
         35                  40                  45
Leu Glu Val Ala Ala Val Val Glu Glu Glu Val Ala Asn Cys Ser
     50                  55                  60
```

```
Ser Ser Glu Val Ile Thr Thr Ala Arg Ser Asp Phe Pro Pro Ser Cys
 65                  70                  75                  80

Cys Ser Ser Asn Tyr Asp Gln Leu Ser Ser Ser Glu Pro Glu Val Val
                 85                  90                  95

Lys Asp Asp Asp Gly Leu Gly Asn Arg Thr Ala Asp Pro Glu Val Glu
             100                 105                 110

Ser Gly Glu Ala Ser Ser Lys Gln Lys Glu Ser His Arg Thr Glu Ala
         115                 120                 125

Arg Glu Ala Thr Lys Leu Asp Asp Gln Asp Tyr Pro Ala Thr Lys Ser
     130                 135                 140

Thr Val Gln Ile Lys Met Pro Ser Asp Ser Glu Ile Glu Glu Phe Phe
145                 150                 155                 160

Ala Val Ala Glu Lys Asp Leu Gln Lys Arg Phe Ser Glu Lys Tyr Asn
                 165                 170                 175

Phe Asp Ile Val Lys Asp Val Pro Leu Lys Gly Arg Tyr Asp Trp Val
             180                 185                 190

Pro Ile Asn Pro
         195
```

CYCLIN-DEPENDENT KINASE INHIBITORS AS PLANT GROWTH REGULATORS

CROSS REFERENCE TO RELATED CASES

This is a continuation-in-part of International application PCT/CA99/00532, filed Jun. 8, 1999, which application is incorporated herein by reference.

FIELD

The disclosure relates to the modification of growth and development of plants through transgenic sense or anti-sense expression of cyclin-dependent kinase inhibitor genes.

BACKGROUND

In eukaryotes including plants, the progression of cell cycle events is regulated by a network of gene products and factors to ensure that this crucial process is initiated as an integral part of the growth and the developmental program, and in response to the external environment. These factors exert their influences on the cell cycle machinery via various pathways. At the center of the machinery lies an enzyme complex consisting of a catalytic subunit, cyclin-dependent protein kinase (CDK), and a regulatory subunit, cyclin. CDKs are a group of related serine/threonine kinases and their activity generally depends on their association with cyclins (Pines, 1995).

Early work disclosed the existence of CDKs in yeast. A CDK called Cdc2 ($p34^{cdc2}$, or CDK1) was identified in fission yeast Schizosaccharomyces pombe (Hindley and Phear, 1984) and a Cdc2 homolog called CDC28 was identified in budding yeast Saccharomyces cerevisiae (Lörincz and Reed, 1984). In yeast, Cdc2 (or CDC28) kinase appears to be solely responsible for regulating the progression of the cell cycle.

Animal cells have evolved several Cdc2-related CDKs in order to achieve more complex regulation at multiple levels. In mammalian cells, seven distinct CDKs and eight types of cyclins have been identified (see review by Pines, 1995). Complexes of these CDKs and cyclins appear to act sequentially at different checkpoints during the cell cycle, while incorporating the input of different developmental and environmental cues.

Plants, like higher animals, have multiple CDKs (Francis and Halford, 1995; Jacobs, 1995) and cyclins (Renaudin et al., 1996). In Arabidopsis thaliana, at least two Cdc2 homologues, Cdc2a and Cdc2b (Ferreira et al., 1991; Hirahama et al., 1991) and as many as twelve cyclins belonging to three groups (Renaudin et al., 1996) have so far been documented. Of the two Cdc2 homologues in A. thaliana, Cdc2a resembles more closely Cdc2 homologues from other species because it has a conserved PSTAIRE motif and is able to genetically complement yeast cdc2 or CDC28 mutants (Ferreira et al., 1991; Hirahama et al., 1991), indicating some functional homology of A. thaliana Cdc2a with the yeast Cdc2 kinase. Expression analyses showed that A. thaliana cdc2a expression was correlated with the "competence" of a cell to divide and preceded the re-entry of differentiated cells into the cell division cycle (Martinez et al., 1992; Hemerly et al., 1993), and expression of a dominant negative cdc2a mutant resulted in cell cycle arrest (Hemerly et al., 1995). A. thaliana Cdc2b is atypical in that it has a PPTALRE motif in place of the PSTAIRE motif. Like cdc2a, cdc2b is also expressed in dividing plant cells. While cdc2a is expressed constitutively throughout the cell cycle, cdc2b is reportedly expressed preferably in S and G2 phases (Segers et al., 1996).

Relatively little is known about the cyclins and other proteins and factors which regulate the activity of CDK-cyclin complexes in plant cells. Results from yeast and mammalian studies have demonstrated multiple pathways, both positive and negative, by which CDK activity can be modulated (Lees, 1995). In addition to binding by a cyclin, for example, activation of CDKs may also involve a CDK-activating kinase (CAK) which itself is a CDK, and CDC25 protein phosphatase.

A new aspect of regulating CDK activity was discovered with the identification of CDK inhibitors (see reviews by Pines, 1995; Sherr and Roberts, 1995; Harper and Ellege, 1996). These small molecular weight proteins are understood to bind stoichiometrically to negatively regulate the activity of CDKs. It has been suggested that these inhibitors may be involved in animal development and cancer, in addition to their role in cell cycle regulation (Harper and Elledge, 1996). A plant CDK inhibitor activity was observed and was suggested to be involved in endosperm development in maize (Grafi and Larkins, 1995).

The activity of CDK inhibitors has been studied in animals. Transgenic mice have been generated lacking p21, p27 and p57 CDK inhibitor genes. The p21 knockout mice are reported to develop normally but are deficient in G1 checkpoint control, such as cell cycle arrest in response to DNA damage (Deng et al., 1995). Analysis of p27 knockout mice from three independent studies show that transgenic mice lacking p27 display larger body size than control mice (Fero et al., 1996; Kiyokawa et al., 1996; Nakayama et al., 1996). The enhanced growth is reportedly due to an increase in cell number (Kiyokawa et al., 1996) and is gene dose-dependent (Fero et al., 1996). In comparison, none of p21 or p57 knockout display enhanced growth. The transgenic mice lacking p57 show a range of developmental defects such as defective abdominal muscles, cleft palate and renal medullary dysplasia (Yan et al., 1997; Zhang et al., 1997). A few developmental defects were observed in p27-/- mice. They include impaired ovarian follicles (thus female sterility), impaired luteal cell differentiation and a disordered estrus cycle. These results reflect a disturbance of the hypothalamic-pituitary-ovarian axis. In comparison, transgenic mice lacking p21 appear to develop normally at both gross anatomic and histologic levels (Deng et al., 1995). In addition, an increase in apoptosis is observed in mice lacking p57. The CDK inhibitor p27 was over-expressed in mouse hepatocytes (Wu et al., 1996), resulting in a general decrease in overall number of adult hepatocytes which result in aberrant tissue organization, body growth and mortality.

Despite the general conservation of basic cell cycle machinery in eukaryotes, the role of plant cell division during plant growth and development is characteristically different from other eucaryotic cells. In many respects, the regulation of plant cell division and growth can be regarded as distinct from other eucaryotic cells. For example, plant cells are not mobile during morphogenesis. Different sets of hormones are involved in modulating plant growth and development. Plant cells are remarkable for their ability to re-enter the cell cycle following differentiation. Also, cell division in plants is continuous, along with organ formation, and plant body size (the number of total cells and size of the cells) can vary dramatically under different conditions. Plants also have an inherent ability to incorporate additional growth into normal developmental patterns, as is illustrated by a study showing that ectopic expression of a mitotic cyclin driven by the cdc2a promoter resulted in a larger but normal root system (Doerner et al., 1996). However, relatively little is known about the connections of the regulatory genes controlling cell division patterns to the cell cycle regulators such as the CDKs and the cyclins in plants (Meyerowitz, 1997).

A few studies of transgenic expression of cell cycle genes in plants are documented using various cell cycle genes other than CDK inhibitors. A heterologous yeast cdc25, a mitotic inducer gene, was introduced into tobacco plants under the control of a constitutive CaMV 35s promoter (Bell et al., 1993). Transgenic tobacco plants showed abnormal leaves (lengthened and twisted lamina, pocketed interveinal regions), abnormal flowers, and also precocious flowering. Analysis of cell size in the root meristem revealed that transgenic plants expressing the yeast cdc25 had much smaller cells (Bell et al., 1993). The wild type cdc2a gene and variants of dominant negative mutations under the control of CaMV 35s promoter have been used to transform tobacco and Arabidopsis plants (Hemerly et al., 1995). Constitutive expression of wild-type and mutant Cdc2a did not significantly alter the development of the transgenic plants. For the dominant negative Cdc2a mutant, it was not possible to regenerate Arabidopsis plants. Some tobacco plants expressing this construct were obtained and they had considerably fewer but much larger cells. These cells, however, underwent normal differentiation. Morphogenesis, histogenesis and developmental timing were unaffected (Hemerly et al., 1995). As mentioned above, ectopic expression of an Arabidopsis mitotic cyclin gene, cyc1At, under the control of the cdc2a promoter increases growth without altering the pattern of lateral root development in Arabidopsis plants (Doerner et al., 1996).

The yeast two-hybrid system has been used to identify the cyclin-dependent kinase inhibitor gene ICK1 from a plant (Wang et al., 1997). ICK1 is different in sequence, structure and inhibitory properties from known mammalian CDK inhibitors. It has been shown that recombinant protein produced from this gene in bacteria is able to inhibit plant Cdc2-like kinase activity in vitro (Wang et al., 1997).

Cytotoxin genes, i.e. genes encoding a protein which will cause cell death, have been tested in transgenic plants for genetic ablation of specific cells or cell lines during development, including RNase (Mariani et al., 1990), DTT (diphitheria toxin) chain A (Thorsness et al., 1991; Czako et al., 1992), Exotoxin A (Koning et al., 1992) and ribosomal inhibitor proteins (U.S. Pat. No. 5,723,765 issued Mar. 3, 1998 to Oliver et al.). Several disadvantages may be associated with the use of cytotoxin genes for modification of transgenic plants, particularly plants of agronomic importance. The action of the cytotoxin may not be specific and may result in non-specific destruction of plant cells. This effect may be the result of diffusion of the cytotoxin, or of non-specific expression of the cytotoxin gene in non-target tissues. Non-specific low-level expression of the cytotoxin may be a difficult problem to overcome, since most tissue-specific promoters have some levels of expression in other tissues in addition to a high level of expression in a particular tissue. Expression of a potent cytotoxin gene even at a low concentration may have a negative impact on growth and development in non-target tissues. The presence of cytotoxic proteins of transgenic origin may also have a negative effect on the marketability of an edible plant, or plant product, even if the cytotoxin is demonstrably benign to consumers.

SUMMARY OF THE DISCLOSURE

Methods are provided for modifying plant or plant cell development using CDK inhibitors. In the context of the disclosure, the word 'development' encompasses a wide variety of biological process, including growth, morphogenesis, multiplication, enlargement, differentiation or maturation of a cell. In one aspect, the provided methods involve transforming a plant cell with a nucleic acid encoding a cyclin-dependent kinase inhibitor polypeptide, or an anti-sense construct complementary to such a nucleic acid, to produce a transformed plant cell; and, growing the transformed plant cell, or progeny of the transformed plant cell, under conditions wherein the cyclin-dependent kinase inhibitor polypeptide, or the anti-sense construct, is expressed in the transformed plant cell or in the progeny of the transformed plant cell. The growing of the transformed plant cell or progeny of the transformed plant cell may be carried out to produce a transformed plant, and the cyclin-dependent kinase inhibitor polypeptide, or anti-sense construct, may be expressed to modify the development of the transformed plant or progeny of the transformed plant.

One embodiment provides methods for using CDK inhibitor genes to modify the growth and development of plant cells and organs. In particular, a method of modifying the development of a plant comprising (i.e. having or including, but not limited to) transforming a plant cell with a nucleic acid encoding a cyclin-dependent kinase inhibitor to produce a transformed plant cell is provided. A plant may then be regenerated from the transformed plant cell under conditions wherein the cyclin-dependent kinase inhibitor is expressed during regeneration or growth of the plant to modify the development of the plant. The nucleic acid encoding the cyclin-dependent kinase inhibitor may be homologous to ICK1, or may be ICK1, respectively encoding a cyclin-dependent kinase inhibitor homologous to ICK1 or ICK1 itself. In particular embodiments, the plant may be *A. thaliana*, or a member of the *Brassica* genus, or a canola variety. The nucleic acid encoding the cyclin-dependent kinase inhibitor may be operably linked to a tissue-specific promoter, such as AP3 or a promoter homologous to AP3. In particular embodiments, the tissue-specific promoter may mediate expression of the nucleic acid encoding the cyclin-dependent kinase inhibitor in petal and/or stamen primordia, and the development of the plant may be modified so that the plant has altered petals and/or is male sterile.

Another aspect provides transgenic plants comprising (i.e. having or including, but not limited to) an expressible heterologous nucleic acid encoding a cyclin-dependent kinase inhibitor, wherein the heterologous nucleic acid is introduced into the plant, or an ancestor of the plant, by the foregoing method. Alternatively, the plants may comprise a nucleic acid encoding a cyclin-dependent kinase inhibitor, and the plant cells may be transformed with an anti-sense nucleic acid complementary to the nucleic acid encoding the cyclin-dependent kinase inhibitor, to produce a transformed plant cell. So that regenerating the plant from the transformed plant cell under conditions wherein the anti-sense nucleic acid is transcribed during regeneration or growth of the plant to inhibit the expression of the cyclin-dependent kinase inhibitor and modify the development of the plant. Plants provided by the disclosure may have a recombinant genome and the heterologous nucleic acid may be integrated into the recombinant genome. Also encompasses herein are plant tissues, such as seeds, comprising a heterologous nucleic acid encoding a cyclin-dependent kinase inhibitor, or an anti-sense construct, that is expressed during the development of a plant from the tissue to modify the development of the plant.

Another aspect of the disclosure provides methods of identifying nucleic acids that encode cyclin-dependent kinase inhibitors, such as nucleic acids homologous to ICK1, that are active in plants to modify the growth or development of the plants.

BRIEF DESCRIPTION OF THE DRAWINGS

FIG. 2 shows the alignment of ICK1 cDNA sequence (SEQ ID NO: 3) with ICK1b (SEQ ID NO: 4) and ICKc (SEQ ID NO: 5).

FIG. 3 shows the cDNA sequence of ICK2 (SEQ ID NO: 6).

FIG. 4 shows the cDNA sequence of ICN2 (SEQ ID NO: 7).

FIG. 5 shows the cDNA sequence of ICN6 (SEQ ID NO: 8).

FIG. 6 shows the cDNA sequence of ICN7 (SEQ ID NO: 9); The nucleotide sequence of *Chenopodium rubrum* CDKI1 (GenBank AJ002173, SEQ ID NO. 15); and, The amino acid sequence of *Chenopodium rubrum* CDKI1 (SEQ ID NO. 16).

FIG. 7 shows the alignment of deduced amino acid sequences of ICK1 (SEQ ID NO: 10), ICK2 (SEQ ID NO: 11), ICN2 (SEQ ID NO: 12), ICN6 (SEQ ID NO: 13), and ICN7 (SEQ ID NO: 14), and a resultant consensus sequence.

FIG. 8 shows deletion mapping in the yeast two-hybrid system of functional regions of ICK1 involved in interactions with Cdc2a and CycD3 (cyclin $_\delta$3) in the two-hybrid system.

BRIEF DESCRIPTION OF THE SEQUENCE LISTING

Figure 1:
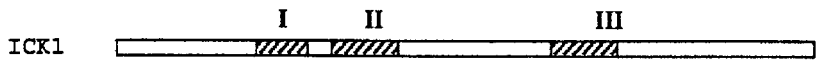
FIG. 1 shows cDNA (Wang et al., 1997) and genomic sequences of ICK1, wherein: (A) shows the genomic organization ICK1. Open bars represent exons and filled bars represent introns; (B) shows features of the cDNA sequence (SEQ ID NO: 1) and deduced amino acid sequence (SEQ ID NO: 2).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO.: 1 shows the nucleic acid sequence and deduced amino acid sequence of ICK1. These sequences are also shown in FIG. 1.

SEQ ID NO.: 2 shows the deduced amino acid sequence of ICK1. This sequence is also shown in FIG. 1.

SEQ ID NO.: 3 shows the nucleic acid sequence of the ICK1 cDNA. This sequence is also shown in FIG. 2.

SEQ ID NO.: 4 shows the nucleic acid sequence of the ICK1b cDNA. This sequence is also shown in FIG. 2.

SEQ ID NO.: 5 shows the nucleic acid sequence of the ICK1c cDNA. This sequence is also shown in FIG. 2.

SEQ ID NO.: 6 shows the nucleic acid sequence of the ICK2 cDNA. This sequence is also shown in FIG. 3.

SEQ ID NO.: 7 shows the nucleic acid sequence of the ICN2 cDNA. This sequence is also shown in FIG. 4.

SEQ ID NO.: 8 shows the nucleic acid sequence of the ICN6 cDNA. This sequence is also shown in FIG. 5.

SEQ ID NO.: 9 shows the nucleic acid sequence of the ICN7 cDNA. This sequence is also shown in FIG. 6.

SEQ ID NO.: 10 shows the deduced amino acid sequence of ICK1. This sequence is also shown in FIG. 7.

SEQ ID NO.: 11 shows the deduced amino acid sequence of ICK2. This sequence is also shown in FIG. 7. SEQ ID NO.: 12 shows the deduced amino acid sequence of ICN2. This sequence is also shown in FIG. 7.

SEQ ID NO.: 13 shows the deduced amino acid sequence of ICN6. This sequence is also shown in FIG. 7.

SEQ ID NO.: 14 shows the deduced amino acid sequence of ICN7. This sequence is also shown in FIG. 7.

SEQ ID NO.: 15 shows the nucleic acid sequence of the CDKI1 cDNA (GenBank AJ002173). This sequence is also shown in FIG. 6.

SEQ ID NO.: 16 shows the deduced amino acid sequence of CDKI1. This sequence is also shown in FIG. 6.

DETAILED DESCRIPTION

Methods are provided for modifying plant or plant cell development. In the context of the disclosure, the word 'development' encompasses a wide variety of biological process, including growth, morphogenesis, multiplication, enlargement, differentiation or maturation of a cell or plant. In one aspect, the methods provided herein involve transforming a plant cell with a nucleic acid encoding a cyclin-dependent kinase inhibitor polypeptide, or an anti-sense construct complementary to such a nucleic acid, to produce a transformed plant cell; and, growing the transformed plant cell, or progeny of the transformed plant cell, under conditions wherein the cyclin-dependent kinase inhibitor polypeptide, or the anti-sense construct, is expressed in the transformed plant cell or in the progeny of the transformed plant cell. A 'CDK inhibitor polypeptide' is any polypeptide capable of inhibiting a CDK, preferably a CDK active during development of a plant or plant cell. The growing of the transformed plant cell or progeny of the transformed plant cell may be carried out to produce a transformed plant, such as by regenerating a plant from a transformed culture or by propagating or growing whole plants from transformed plant parts. The cyclin-dependent kinase inhibitor polypeptide, or anti-sense construct, may be expressed to modify the development of the transformed plant or progeny of the transformed plant. The term 'progeny', with reference to a plant, includes progeny produced sexually or asexually (for example by tissue culture-based propagation). The term 'growing' with reference to the transformed cells or plants includes all methods for growing and propagating cells or plants, such as tissue culture or horticultural means of propagating plants or plant parts.

In the following detailed description, various examples are set out of particular embodiments, together with experimental procedures that may be used to implement a wide variety of modifications and variations in the practice of the present invention.

In the context of the present disclosure, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

For the present disclosure, promoters may be used that provide for preferential gene expression within a specific organ or tissue, or during a specific period of development. For example, promoters may be used that are specific for leaf (Dunsmuir, et al *Nucleic Acids Res*, (1983) 11:4177–4183), root tips (Pokalsky, et al *Nucleic Acids Res*, (1989) 17:4661–4673), fruit (Peat, et al *Plant Mol. Biol*, (1989) 13:639–651; U.S. Pat. No. 4,943,674 issued 24 Jul. 1990; International Patent Publication WO-A 8 809 334; U.S. Pat. No. 5,175,095 issued 29 Dec. 1992; European Patent Application EP-A 0 409 629; and European Patent Application EP-A 0 409 625) embryogenesis (U.S. Pat. No. 5,723,765 issued 3 Mar. 1998 to Oliver et al.), or young flowers (Nilsson et al. 1998). Such promoters may, in some instances, be obtained from genomic clones of cDNAs. Depending upon the application, those skilled in this art may choose a promoter for use in the invention that provides a desired expression pattern. Promoters demonstrating preferential transcriptional activity in plant tissues are, for example, described in European Patent Application EP-A 0 255 378 and International Patent Publication WO-A 9 113 980. Promoters may be identified from genes which have a differential pattern of expression in a specific tissue by screening a tissue of interest, for example, using methods described in U.S. Pat. No. 4,943,674 and European Patent Application EP-A 0255378. The disclosure herein includes examples of this embodiment, showing that plant tissues and organs can be modified by transgenic expression of a plant CDK inhibitor.

Non-dividing plant cells may tolerate low level expression of CDK inhibitors, such as ICK1, in non-targeted tissues. Thus, the invention may be practiced in some embodiments using tissue specific promoters operably linked to CDK inhibitor encoding sequences, even when the promoter mediates a tolerable basal level of expression in other tissues.

Various aspects of the present disclosure encompass nucleic acid or amino acid sequences that are homologous to other sequences. As the term is used herein, an amino acid or nucleic acid sequence is "homologous" to another sequence if the two sequences are substantially identical and the functional activity of the sequences is conserved (for example, both sequences function as or encode a cyclin-dependent kinase inhibitor; as used herein, sequence conservation or identity does not infer evolutionary relatedness). Nucleic acid sequences may also be homologous if they encode substantially identical amino acid sequences, even if the nucleic acid sequences are not themselves substantially identical, for example as a result of the degeneracy of the genetic code.

Two amino acid or nucleic acid sequences are considered substantially identical if, when optimally aligned, they share at least about 70% sequence identity. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman (1981) *Adv. Appl. Math* 2: 482, the homology alignment algorithm of Needleman and Wunsch (1970) *J. Mol. Biol.* 48:443, the search for similarity method of Pearson and Lipman (1988) *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990), *J. Mol. Biol.* 215:403–10 (using the published default settings). Software for performing BLAST analysis may be available through the National Center for Biotechnology Information (NCBI) at their Internet site. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff (1992) *Proc. Natl. Acad. Sci. USA* 89: 10915–10919) alignments (B) of 50, expectation (E) of 10, M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

An alternative indication that two amino acid sequences are substantially identical is that one peptide is specifically immunologically reactive with antibodies that are also specifically immunoreactive against the other peptide. Antibodies are specifically immunoreactive to a peptide if the antibodies bind preferentially to the peptide and do not bind in a significant amount to other proteins present in the sample, so that the preferential binding of the antibody to the peptide is detectable in an immunoassay and distinguishable from non-specific binding to other peptides. Specific immunoreactivity of antibodies to peptides may be assessed using a variety of immunoassay formats, such as solid-phase ELISA immunoassays for selecting monoclonal antibodies specifically immunoreactive with a protein (see Harlow and Lane (1988) *Antibodies, A Laboratory Manual*, Cold Spring Harbor Publications, New York).

The cyclin-dependent kinase inhibitors of the present invention, and the genes encoding those inhibitors, may include non-naturally occurring sequences, such as functionally active fragments of naturally occurring sequences. For example, fragments of ICK1, or amino acid sequences homologous to those fragments, that have cyclin-dependent kinase inhibitory activity may be used in some embodiments. Methods are provided for identifying such fragments, for example by deletion mapping of active cyclin-dependent kinase inhibitors. As used herein the term "cyclin-dependent kinase inhibitor" therefore includes any polypeptide capable of functioning to inhibit a cyclin-dependent kinase and may be used to modify the growth or development of the plant, the invention similarly encompasses nucleic acid sequences encoding such polypeptides.

As used herein to describe nucleic acid or amino acid sequences the term "heterologous" refers to molecules or portions of molecules, such as DNA sequences, that are artificially introduced into a particular host cell. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events.

The specificity of a CDK inhibitor may be assayed in vivo. For example, the ICK1 coding sequence was fused to a known promoter which directed gene expression in pollen but not in stamen primordia. The transformants are normal and fertile. This result indicates that in specific embodiments, expression of ICK1 is not generally toxic to tissues other than the target tissue. Phenotypes may be obtained, for example with the exemplified AP3-ICK1 transformants, that are due to specific action of the CDK inhibitor, such as ICK1 protein, on cell division. In such embodiments, the CDK inhibitor, such as ICK1, may be used as a specific tool to modify growth or development of meristematic tissues without materially affecting other processes.

In some embodiments, there may be important advantages to using a sequence encoding a CDK inhibitor for genetic engineering in plants, particularly to control selected cell lineages, rather than using genes encoding cytotoxins. In accordance with the invention, the CDK inhibitor action may be made to be specific only to certain cells, avoiding the non-specific destruction of plant cells. This specificity may be achieved partly because non-dividing plant cells in non-targeted tissues may have better tolerance of low level expression of a CDK inhibitor than a cytotoxin. Thus, in accordance with the invention it may be possible to use tissue specific promoters for expressing CDK inhibitors when such promoters still have a tolerable basal level of expression in other tissues. This may usefully expand the range of promoters available for use in the invention, since most tissue-specific promoters have some levels of expression in other tissues in addition to a high level of expression in a particular tissue. In contrast, expression of a potent cytotoxic gene in one tissue, even at a low concentration, can have a negative impact on growth and development in other tissues.

In an alternative aspect, the down-regulation of CDK inhibitors, such as ICK1, may be used to enhance growth during plant development. Such growth enhancement may be tissue-specific. For example, anti-sense oligonucleotides may be expressed to down-regulate expression of CDK inhibitors. The expression of such anti-sense constructs may be made to be tissue-specific by operably linking anti-sense encoding sequences to tissue-specific promoters. Anti-sense oligonucleotides, including anti-sense RNA molecules and anti-sense DNA molecules, act to block the translation of mRNA by binding to targeted mRNA and inhibiting protein translation from the bound mRNA. For example, anti-sense oligonucleotides complementary to regions of a DNA sequence encoding a CDK inhibitor, such as ICK1, may be expressed in transformed plant cells during development to down-regulate the CDK inhibitor. Alternative methods of down-regulating CDK inhibitor gene expression may include the use of ribozymes or other enzymatic RNA molecules (such as hammerhead RNA structures) that are capable of catalyzing the cleavage of RNA (as disclosed in U.S. Pat. Nos. 4,987,071 and 5,591,610). The mechanism of ribozyme action generally involves sequence specific hybridization of the ribozyme molecule to complementary target RNA, followed by endonucleolytic cleavage.

*Arabidopsis thaliana* "Columbia" may be used as a convenient model system for identifying CDK inhibitors that are useful in various embodiments. *Arabidopsis* plants are generally grown in pots placed in growth chambers (20° C. 16 h/8 h of day/night). Other plants may also of course be used in various embodiments, in accordance with known growth and transformation techniques.

Yeast two-hybrid cloning and assay techniques may be used to identify and assess CDK inhibitors useful in the disclosed systems. For example, a cDNA library may be made using poly (A) mRNA isolated from whole plants at different stages of development and cloned in a suitable vector, such as Gal4 TA-(transcription-activation domain) pPC86 (Chevray and Nathans, 1992; available from GIBCO/BRL Life Technologies) or pBI771- a modified pPC86 (Koholmi et al., 1997). The cDNA of the gene (such as cdc2a, cyclin $_\delta$2 and cyclin $_\delta$3) to be used for screening the library may be cloned in a suitable vector, such as the Gal4 DB-(DNA-binding domain) vector. The yeast strain, such as YPB2 or MaV203, harboring the construct may be transformed using the library DNA.

In one example, for analysis of Cdc2a interactions, a total of $1.8 \times 10^7$ transformants were subjected to two-hybrid selection on supplemented synthetic dextrose medium lacking leucine, tryptophan and histidine but containing 5 mM 3-amino-1,2,4-triazole. The selected colonies were assayed for $_\beta$-galactosidase activity using standard methods. DNAs were isolated from positive clones and used to transform *E. coli*. Clones harboring the TA-fusion cDNAs were identified by PCR and plasmids were then isolated for DNA sequencing (Wang et al., 1997).

Interactions in the yeast two-hybrid system may, for example, be analyzed by either filter assay (Chevray and Nathans, 1992) using X-gal as the substrate or by a quantification assay using ONPG (ortho-nitrophenyl-beta-D-galactoside) as the substrate (Reynolds and Lundlad, 1994). Three or more independent transformants may be used for each interaction.

Standard methods are available for the preparation of constructs for use in identifying and characterizing CDK inhibitors useful in various embodiments. General molecular techniques may for example be performed by procedures generally described by Ausubel et al. (1995). Alternative equivalent methods or variations thereof may be used in accordance with the general knowledge of those skilled in this art.

In one example, the AP3 promoter was cloned by the polymerase chain reaction (PCR) from *Arabidopsis thaliana* "Columbia" genomic DNA, on the basis of the published sequence (Irish and Yamamoto, 1995; GenBank Accession U30729). The promoter was cloned in a modified binary vector pBI121 (Clontech). ICK1 cDNA (SEQ ID NO: 1; Wang et al., 1997) was similarly amplified by PCR and transcriptionally fused with the AP3 promoter and the chimeric gene ends with a nopaline synthase terminator. As a comparison and to determine the effect of ICK1 on differentiated cells such as pollen, the same ICK1 nucleotide sequence used in AP3-ICK1 fusion was used in fusion with a *Brassica rapa* (*B. campestris*) anther-specific promoter Bgp1 (Xu et al. 1993; GenBank Accession X68210). The Bgp1 promoter has been shown to be able to direct a high level of GUS (beta-glucuronidase) gene expression in the pollen and tapetum of transgenic *Arabidopsis* plants (Xu et al., 1993). The resulting plasmids were introduced into *Agrobacterium tumefaciens* strain GV3101 (bearing helper plasmid pMP90; Koncz and Schell 1986).

In accordance with various aspects of the invention, plant cells may be transformed with heterologous nucleic acids. In this context, "heterologous" denotes any nucleic acid that is introduced by transformation. Transformation techniques that may be employed include plant cell membrane disruption by electroporation, microinjection and polyethylene glycol based transformation (such as are disclosed in Paszkowski et al. *EMBO J.* 3:2717 (1984); Fromm et al., *Proc. Natl. Acad. Sci. USA* 82:5824 (1985); Rogers et al., *Methods Enzymol.* 118:627 (1986); and in U.S. Pat. Nos. 4,684,611; 4,801,540; 4,743,548 and 5,231,019), biolistic transformation such as DNA particle bombardment (for example as disclosed in Klein, et al., *Nature* 327: 70 (1987); Gordon-Kamm, et al. "The Plant Cell" 2:603 (1990); and in U.S. Pat. Nos. 4,945,050; 5,015,580; 5,149,655 and 5,466,587); *Agrobacterium*-mediated transformation methods (such as those disclosed in Horsch et al. *Science* 233: 496 (1984); Fraley et al., *Proc. Nat'l Acad. Sci. USA* 80:4803 (1983); and U.S. Pat. Nos. 4,940,838 and 5,464,763).

Transformed plant cells may be cultured to regenerate whole plants having the transformed genotype and displaying a desired phenotype, as for example modified by the expression of a heterologous CDK inhibitor during growth or development. A variety of plant culture techniques may be used to regenerate whole plants, such as are described in Gamborg and Phillips, "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., *Ann. Rev. of Plant Phys.* 38:467 (1987).

Standard techniques may be used for plant transformation, such as transformation of *Arabidopsis*. In one example, the AP3-ICK1 and Bgp1-ICK1 constructs were tested in *A. thaliana* by in planta transformation techniques. Wild type (WT) *A. thaliana* seeds of ecotype "Columbia" were planted in 4" pots containing soil and plants grown in a controlled growth chamber or greenhouse. The vacuum infiltration method of in planta transformation (Bechtold et al., 1993) was used to transform *A. thaliana* plants with overnight culture of *A. tumefacian* strain GV3101 bearing both the helper nopoline plasmid and the binary construct containing the described chimeric gene. pMP90 is a disarmed Ti plasmid with intact vir region acting in trans, gentamycin and kanamycin selection markers as described in Koncz and Schell (1986). Following infiltration, plants were grown to maturity and seeds (T1) were collected from each pod individually. Seeds were surface-sterilized and screened on selective medium containing 50 mg/L kanamycin with or without 200–300 mg/L timentin. After about four weeks on selection medium, the non-transformed seedlings died. The transformed seedlings were transferred to soil in pots. Leaf DNA was isolated (Edwards et al., 1991) and analyzed by PCR for the presence of the DNA insertion. Genomic DNA was also isolated and used in Southern hybridization (Southern, 1975) to determine the copy number of the inserted sequence in a given transformant. To determine the segregation, T2 seeds were collected from T1 plants. Wherever the T1 plant was male sterile, crosses were made using the WT *A. thaliana* pollen to obtain seeds. As described, T2 seeds were surface-sterilized and screened on selective medium.

Alternative embodiments may make use of techniques for transformation of *Brassica*. Such as transformation of *B. napus* cv. Westar and *B. carinata* cv. Dodolla by co-cultivation of cotyledonary petioles or hypocotyl explants with *A. tumefaciens* bearing the plasmids described herein. Transformation of *B. napus* plants may, for example, be performed according to the method by Moloney et al. (1989). Modifications of that method may include the introduction of a 7-day explant-recovery period following co-cultivation, on MS medium with the hormone benzyladenine (BA), and the antibiotic timentin for the elimination of *Agrobacterium*. Transformation of *B. carinata* plants may be performed according to the method by Babic et al. (1998). Cotyledonary petiole explants may be dipped in suspension of *Agrobacterium* bearing the desired constructs and placed on 7-cm filter paper (Whatman no. 1) on top of the regeneration medium for 2 days. After co-cultivation, explants may be transferred onto the selection medium containing 50 mg/L kanamycin. Regenerated green shoots may first be transferred to a medium to allow elongation and then to a rooting medium all containing 50 mg/L kanamycin. Putative transformants with roots (T0) may be transferred to soil. Genomic DNA may be isolated from developing leaves for PCR and Southern analyses. Seeds (T1) from transgenic plants may then be harvested.

Transgenic plants may be observed and characterized for alteration of traits such as petals, male sterility and ability to set seeds. For example, to determine the development of floral organs, flowers at different stages of development may be dissected and examined under a stereomicroscope. Floral samples may also be examined using scanning electron microscope for more defined morphology of floral organ meristems and their development.

Genomic clones of sequences encoding putative CDK inhibitors may be cloned using standard techniques. For example, to clone a genomic ICK1 encoding sequence, genomic DNA may be isolated from two-week old *A. thaliana* seedlings (according to the procedure described by Lohdi et al., 1994). In one example, the genomic sequence spanning the ICK1 cDNA sequence (SEQ ID NO: 1) was amplified by 30 cycles of PCR using sequence-specific primers with incorporated restriction sites. Pfu DNA polymerase (Stratagene), which has a higher replication fidelity than the Taq DNA polymerase, may be used. The amplified DNA fragment may be cloned into a suitable vector, such as pGEM5Zf(+) (Promega). Plasmids may then be purified and sequenced.

In one example, an ICK1 cDNA isolated from the two hybrid screening was cloned in frame into pBI786, a modified $His_6$-tagged vector derived from pRSETB (Invitrogen) (Wang et al., 1997). Recombinant $His_6$-ICK1 was purified from *E. coli* using Ni-NTA agarose resin (QIAGEN) according to manufacturer's instructions except that the final washing was with buffer D, pH 6.0 and the protein was eluted with 2 ml buffer D, pH 4.0. The eluent was renatured by diluting with 10× volume of a renaturing buffer (10 mM Tris pH 7.5, 500 mM NaCl, 400 mM arginine HCl, 20 $\mu$M $MgCl_2$, 20 $\mu$M ZnAc and 0.1% Tween 20) and dialysed in the same buffer (500 ml per 2 ml sample) at 4° C. overnight. The protein samples may be concentrated with Filtron 10K concentrators. The sample was then dialyzed at 4° C. for 3 h against 1000 volumes of the kinase assay buffer (see below) containing 0.4 mM DTT and each (0.4 $\mu$g/ml) of the protease inhibitors soybean trypsin inhibitor, antipain and apotinin. The protein was stored at −80° C.

Kinase assays may be useful in some aspects, for example to assay the function of CDK inhibitors on particular kinases. For example, kinases may be purified from *A. thaliana* tissues or cultured *B. napus* cells. Plant materials may be homogenized in 2 mls per gram tissue of ice cold extraction buffer consisting of 25 mM Tris pH 8.0, 100 mM NaCl, 10 mM DTT, 5 mM NaF, 1 mM $Na_3VO_4$, 1 mM $\beta$-glycerophosphate, 2.5 mM EDTA, 400 $\mu$g/ml AEBSF [4-(2-aminoethyl)-enzensulfonyl fluoride], 1 $\mu$g/ml leupeptin and 1 $\mu$g/ml pepstatin. The homogenate was centrifuged at 12,000 g at 4° C. for 30 min. The supernatants may be used to purify Cdc2-like protein kinases using $p13^{suc1}$-conjugated agarose beads (Oncogene Sciences). The required amount of supernatant (150 $\mu$g protein for each reaction) was added to the beads and tumbled at 4° C. for 2 h. The beads may be washed twice in a washing buffer consisting of 50 mM Tris pH 7.4, 250 mM NaCl, 0.1% NP-40, 2.5 mM EDTA, 1 mM DTT and inhibitor cocktail of (in final concentrations) 10 $\mu$g/ml apotinin, 10 $\mu$g/ml antipain, 10 $\mu$g/ml soybean trypsin inhibitor, 10 mM $\beta$-glycerophosphate, 1 mM NaF and 0.2 mM $Na_3VO_4$. Beads may then be washed twice in the kinase assay buffer (50 mM Tris pH 7.4, 10 mM $MgCl$, 2 mM EGTA, 2 mM DTT and the inhibitor cocktail). For inhibition assays, the recombinant protein was added to the reactions and incubated (tumbling slowly) for 1.5 h at 4° C. The kinase reaction was initiated by adding 1 $\mu$g/$\mu$l histone H1 (Sigma), 25 $\mu$M ATP and 0.05 $\mu$Ci/ul $^{32}P$-$\gamma$-ATP (final concentrations), and stopped after 20 min incubation by adding the sample buffer. Denatured supernatant was resolved by SDS-PAGE.

RNA isolation and northern blotting analysis may be useful in various embodiments. For example, to analyse ICK1 expression during plant development, various tissues may be taken from *Arabidopsis* plants. To analyse the effects of ABA and low temperature, seedlings may be treated as described (Wang et al., 1995). Briefly, seedlings (12 days) grown in pots may be cleared of soil with water, then floated in 0.1× strength MS medium without sucrose and hormones. Low temperature treatment was at 5° C. for 24 h. ABA treatment was carried out in a solution containing 50 $\mu$M ABA. Seedling samples may be removed after various treatment times. Total RNA was isolated using TRIzol reagent (GIBCO BRL). For northern analysis, the indicated amount of RNA was fractionated in a 1.2% agarose gel and transferred onto Hybond-N+ nylon membrane (Amersham). The RNA was crosslinked to the membrane by UV-light (Stratalinker, Stratagene) and hybridized with $^{32}P$-labeled probes. The membranes may be wrapped and used to expose Hyperfilm MP (Amersham) film. Membranes may be stripped by treating with a boiling solution of 0.1× SSC and 0.1% SDS for 5 min. Quantification of hybridized signal was performed using Molecular Dynamics PhosphorImager and the accompanying software.

In vitro binding assays may be useful in various aspects, for example to assay the interaction of a CDK inhibitor, or fragments of a CDK inhibitor, and a particular kinase. As an example of such an approach, $^{35}S$-Met labeled Cdc2a, CycD3 and ATMPK2 proteins may be expressed from a T7 promoter construct using an in vitro coupled rabbit reticulocyte transcription/translation system ('TNT', Promega). $Ni^+$-NTA beads (Qiagen) may be equilibrated and blocked in NETN buffer lacking EDTA (NTN) (Bai et al., 1996), and supplemented with 2 mg/ml BSA. Equilibrated beads may be incubated with $His_6$-ICK1 (5 $\mu$g for each 10 $\mu$l beads) in 1 ml of NTN buffer for 2 h with tumbling at 10° C. followed by washing with 2×1 ml NTN buffer. Binding experiments may be carried out in a total volume of 100 $\mu$l NTN containing 10 $\mu$l beads, plus 5 $\mu l$ $^{35}S$-Met labeled protein. The binding reaction was incubated at 10° C. for 2 h, followed by washing with 3×0.5 ml NTN buffer. Washed beads may be eluted with 10 $\mu$l SDS-containing denaturing buffer at 100° C. for 5 min, and bound $^{35}S$-Met labeled proteins analyzed by SDS-PAGE. Gels may be imbibed with a fluorography enhancer ('Amplify', Amersham) prior to drying and exposure to X-ray film.

Deletion constructs may be useful for domain mapping to determine the functional domains of a CDK inhibitor. For example, N-terminal deletion constructs of ICK1 were made using cDNAs with deletions of various lengths from the N-terminal end. The C-terminal deletion constructs were prepared by PCR using Pfu DNA polymerase with sequence-specific primers and the resulting DNA fragments were cloned into the yeast two-hybrid vector pBI771 (Kohalmi et al., 1997). The deletion clones may be verified by DNA sequencing. The constructs may be used to transform a suitable yeast strain. In one such example, yeast strain YPB2 harboring either cdc2a or CycD3 cloned in the BD- (binding domain) vector was transformed with deletion constructs. Interactions in the yeast two-hybrid system may then, for example, be analyzed by X-gal filter assay (Chevray and Nathans, 1992) and by liquid culture assays for relative $\beta$-galactosidase activity (for example using the modified procedure of Reynolds and Lundlad, 1994). Three or more independent transformants may be used for each interaction.

Sequence Analyses: Sequence analyses, including determination of sequence homology, may be performed using a variety of software, such as LASERGENE (DNASTAR). Database searches may also use a variety of software tools, such as the BLAST program (NCBI).

Analysis of CDK inhibitor cDNA Clones and Genomic Sequences: The yeast two-hybrid system (Fields and Song, 1989; Kohalmi et al., 1997) may be used to identify genes, such as ICK1, that encode inhibitor proteins able to interact with the plant cyclin-dependent kinases, such as Cdc2 Kinase, for use in aspects of the present invention. For example, among the 68 ICK (Interactors of Cdc2 Kinase) clones identified using Cdc2a as the bait in a yeast two hybrid system (Wang et al., 1997), 55 represented various lengths of ICK1, 7 of ICK2 and 6 of ICK3. A contig sequence for homologous clones disclosed by the yeast two hybrid assay may be used, as was the contig sequence for ICK1 cDNA (Wang et al., 1997), to search cDNA and genomic databases at internet sites such as those maintained by NCBI and Stanford (the AtDB database), for sequences homologous to those identified by the two-hybrid screen. Two EST clones homologous to the ICK1 cDNA sequence have been identified in this way. A clone designated 96D15T7 possessed an extra 5' sequence to that of the contig assembled from the two-hybrid cDNA clones. A search of the AtDB database using ICK1 cDNA (SEQ ID NO: 1) or genomic sequences indicates that the ICK1 gene sequence is located in a BAC (bacterial artificial chromosome) genomic clone F26B6 (GenBank AC003040), which is 128 kb in length and is identified as being located on *Arabidopsis thaliana* chromosome II between cM 35–45 (see the AtDB maintained by Stanford, clone F26B6).

Specific PCR primers may be synthesized and used to clone the genomic sequence spanning the entire coding region of a CDK inhibitor gene. For ICK1, three independent clones harboring the genomic sequence were identified in this way, sequenced and found to be identical. Alignment of ICK1 genomic sequence with the ICK1 cDNA sequence (SEQ ID NO: 1; GenBank U94772, Wang et al., 1997) reveals three introns. The genomic sequence in the exon regions is identical to the contig of cDNA clones except at nucleotide position 318, which is a T instead of a G as in the reported cDNA sequence (Wang et al., 1997; a majority of the cDNA clones had a G, while other clones had a T at this position). The existence of a T at this position in genomic DNA was verified by sequencing additional genomic clones. The longest open reading frame in the ICK1 cDNA sequence (SEQ ID NO: 1) predicts a polypeptide of 191 amino acids (SEQ ID NO: 2; Wang et al., 1997). There is an in-frame translation STOP codon 12 nucleotides upstream of the first ATG. In addition, an in-frame translation termination codon was found 30 nucleotides down stream of the predicted termination codon.

CDK inhibitor in vitro assays: In vitro kinase assays may be used to demonstrate that a recombinant putative CDK inhibitor, such as ICK1 protein, is an effective inhibitor of plant Cdc2-like kinases. Plant CDK inhibitors may not inhibit CDK from mammalian and yeast cells (Wang et al., 1997). For example, recombinant ICK1 is effective in vitro in inhibiting the histone H1 kinase activity of $p13^{suc1}$-associated kinases from cultured cells of heterologous *Brassica napus*. In addition, it also inhibits the activity of such kinases from *A. thaliana* seedlings, leaves and floral tissues in vitro.

Expression of CDK inhibitors: The expression of a CDK inhibitor in particular plant tissues may be assayed to determine, for example, whether that CDK inhibitor will have utility as a division or growth modulator when expressed in such tissues. For example, the expression of ICK1 was analyzed in several different plant tissues. In general, the transcript abundance of ICK1 was relatively low and showed low degrees of variation compared with the housekeeping genes such as TUA4 (a tubulin-$\alpha$ gene) and GAPDH (glyceraldehyde phosphate dehydrogenase) of *A. thaliana*. When leaves from plants of different ages were compared, the ICK1 level in sample L5 (for leaves of 5-week plants) was slightly higher. To verify the functional role of a putative CDK inhibitor in such tissues, the CDK activity may also be assayed.

Regulation of CDK inhibitors by phytohormones and environmental conditions: Putative CDK inhibitors may be assayed for suitable CDK inhibitor activity for use in certain methods of the invention by a variety of tests. For example, induction of expression of the putative CDK inhibitor gene by abscisic acid (ABA), a phytohormone known to inhibit plant growth (Evans, 1984), and at low temperatures. For example, expression of the putative CDK inhibitor gene, such as ICK1, in seedlings, such as *A. thaliana* seedlings, may be analyzed in response to treatments with ABA. For ICK1, data from an example assay showed that after 24 h, ABA and low temperature treatments increased ICK1 transcript levels to about 3 times that of the control (no ABA and at 22° C.) in 2-week seedlings. The expression of the putative CDK inhibitor gene may be quantified. For ICK1, a correlation coefficient was obtained for the relationship of cdc2a level, ICK1 level and cdc2a/ICK1 ratio with the Cdc2-like kinase activity. The level of cdc2a expression was correlated with the level of Cdc2-like histone H1 kinase activity. The level of ICK1 expression exhibited a weak negative correlation with kinase activity. The correlation coefficient for the cdc2a/ICK1 ratio with Cdc2-like kinase activity was similar to that for cdc2a with Cdc2-like kinase activity. Such results are consistent with CDK (in this example Cdc2 kinase) inhibitor activity in plant cells.

Direct Interaction of ICK1 with Both Cdc2a and CycD3: CDK inhibitors for use in various aspects of the invention may be identified using a yeast two hybrid screening protocol with a variety of bait fusion protein sequences. For example, ICK1 was independently cloned in a screen using *A. thaliana* CycD3 as the bait, indicating that ICK1 interacts with CycD3 in the two hybrid assay. To provide evidence confirming the interaction of a CDK inhibitor with a target protein of interest, further binding assays may be conducted. For example, to test the interactions of ICK1, cdc2a and CycD3 cDNAs were transcribed and translated in an in vitro system. In vitro expressed Cdc2a and CycD3 proteins were incubated with recombinant $His_6$-ICK1 protein expressed in *E. coli*. Cdc2a and CycD3 bound to Ni-NTA beads only after they were incubated with recombinant ICK1. The amount of CycD3 bound to recombinant ICK1 protein was more than the control protein ATMPK2 which showed little binding despite the much higher input used. These results demonstrate that ICK1 is able to interact directly with both Cdc2a and CycD3. Similar assays may be used to identify CDK inhibitors capable of interacting with other cellular targets.

Mapping the Domains for ICK1 Interaction with Cdc2a and CycD3: The regions of a CDK inhibitor that are functionally involved in interactions with other proteins may be mapped by deletion mapping using a variety of techniques, such as the yeast two-hybrid system and variations thereof. Such in vitro assay results may be verified by in vivo tests, since the persistence of interactions in the two hybrid system may be affected by possible alterations in functionality of plant proteins expressed in yeast. As an example of an in vitro assay, to determine the functional significance of the C-terminal domain and other regions of ICK1, three N-terminal and three C-terminal deletion mutants were assessed for their interactions with Cdc2a and CycD3 in the two-hybrid system. Overall, $_\beta$-galactosidase marker gene activation in the two hybrid system was stronger for the interaction of all ICK1 constructs with CycD3 compared to Cdc2a, indicative of a stronger or more persistent interaction between ICK1 and CycD3 in the two-hybrid system. Major shifts in $_\beta$-galactosidase activity were observed when amino acid regions 3–72, 109–153 and 176–191 were deleted. An increase in activity was observed upon deletion of amino acids 3–72. In pairwise comparison, the deletion of amino acid regions 3–72, 73–108, 163–175 or 153–162 had comparable effects on the interactions of ICK1 with Cdc2a versus CycD3, as reflected by the marker gene expression, while the deletions of amino acid regions 109–153 and 176–191 had clearly differential effects. The most significant reduction in $_\beta$-galactosidase activity for the interaction of ICK1 with CycD3 resulted from the deletion of amino acids 109–153, whereas the deletion of amino acids 176–191 had a more detrimental effect on the interaction with Cdc2a. The functional importance of a portion of a CDK inhibitor may also be assayed by analyzing the portion of cDNA required for the recovery of clones by each bait construct in the two hybrid system. For example, the region spanning amino acids 109–153 of ICK1 for its interaction with CycD3 was supported by the analysis of the minimum cDNA length required for the recovery of clones by each bait construct. With CycD3 as the bait, the shortest ICK1 cDNA was N-terminal deleted for amino acids 1–129, while with Cdc2a, seven clones with further deletions extending to amino acid 154 were also isolated. Thus, deletions extending beyond amino acid 130 rendered these clones unrecoverable by the two-hybrid screening using CycD3 as the bait. Taken together, the results indicate that, while the C-terminal domain (containing the consensus sequence with p27$^{Kip1}$) is most important for the interaction with Cdc2a, the amino acid region 109–153 perhaps with the C-terminal domain is important for the interaction with CycD3.

One aspect of the invention utilizes functionally important regions of a CDK inhibitor, such as ICK1, as components of novel CDK inhibitors. As outlined above, the functionally important regions of a CDK inhibitor may be determined through routine assays. Alternatively, randomly selected portions of a CDK inhibitor may be selected for use in routine assays to determine whether the selected region is capable of functioning as a CDK inhibitor in the context of the present invention. In various embodiments, regions of ICK1 may be used, such as the 109–153 region and/or the 163–191 region, with or without additional regions from ICK1 or other CDK inhibitors, provided the recombinant protein meets the functional requirements of the present invention (which may be determined through routine screening of functionality).

*Arabidopsis* transformation with ICK1 constructs: A wide variety of transformation techniques may be used in accordance with the invention to introduce CDK inhibitor genes into plants. In one aspect, methods of assaying heterologous CDK inhibitor function in a model plant, such as *Arabidopsis*, are provided. For such assays, in one embodiment, transformation may be carried out by infiltration. For example, seeds (T1 generation) collected from infiltrated *Arabidopsis* plants may be surface-sterilized and placed onto MS medium containing 50 $\mu$g/ml kanamycin. The antibiotic timentin may also be included in the medium to prevent any bacterial growth, which could occur due to carrier-over from the infiltration. The vast majority of germinating seedlings will not be transformed, and will became pale and eventually stop growing, transformed seedlings will be green and display normal growth due to the presence of the selectable marker gene. After 4–5 weeks in the selection medium, transformants may be transferred to soil in pots. In the exemplary embodiment, the presence of the DNA insertion was confirmed by extracting the genomic DNA and then using it for PCR amplification. In one example, while the non-transformed wild-type plant gave a negative signal, all twelve (12) plants selected for their resistance to kanamycin were positive for transforming DNA.

Effect of AP3-ICK1 chimeric gene on petal and stamen development: Various aspects of the invention may be used to obtain a wide variety of phenotypic variations in plant morphology or other characteristics. For example, transformed *A. thaliana* plants carrying the AP3-ICK1 construct displayed a range of phenotypes with regard to petal and stamen morphology (Table 1). Such variation may be due to the insertion, in alternative embodiments, of the CDK inhibitor gene into different sites of the plant genome. In the example of modified petal development using ICK1, the plants may be classed into three groups: (1) no visible petals, (2) visible petals but reduced size and (3) visible petals with no apparent difference to those of non-transformed plants (Table 1). In terms of fertility, eleven out of twelve plants were male sterile. These results demonstrate that tissue-specific expression of ICK1 may be used to produce plants with modified petals and/or with male sterility. In some embodiments, the transgenic plants with male sterility may set seeds after pollination, using pollen from non-transformed plants, indicating that the female reproduction system is unaffected in these male sterile plants. Apart from these specific modifications, these transgenic plants otherwise grew and developed normally.

TABLE 1

Summary of phenotypes of *A. thaliana* plants transformed with AP3-ICK1 chimeric gene.

| Transformant | Petal | Sterility | Seed setting with WT pollen |
| --- | --- | --- | --- |
| #1 | Reduced size | Sterile | Yes |
| #2 | No visible petals | Sterile | Yes |
| #3 | Normal | Fertile | self-fertile |
| #4 | Reduced size | Sterile | Yes |
| #5 | Reduced size | Sterile | Yes |
| #6 | No visible petals | Sterile | Yes |
| #7 | Reduced size | Sterile | Yes |
| #8 | No visible petals | Sterile | Yes |
| #9 | No visible petals | Sterile | Yes |
| #10 | No visible petals | Sterile | ND[1] |
| #11 | No visible petals | Sterile | Yes |
| #12 | No visible petals | Sterile | Yes |

[1]Not determined

Co-Inheritance of the inserted gene and phenotype: T2 plants may be studied to determine the segregation of the inserted gene and also to verify whether the particular phenotype is co-inherited with the inserted gene. For example, T2 seeds of ICK1 transformants were sterilized and placed onto the selective medium. In one such assay, T2 seeds of one transformant (#2) showed 1:1 ratio of segregation between resistant (99) versus non-resistant (102) seedlings. As transformant #2 was male sterile, the T2 seeds were obtained by crosses using wild type pollen. This ratio indicates that there is one insertion in the genome of this transformant. As expected, T2 plants displayed the same phenotype as the corresponding T1 plants.

Increased ICK1 expression in young floral buds is associated with phenotype changes: To analyze ectopic ICK1 expression in floral buds of transgenic AP3-ICK1 Arbidopsis plants, young floral buds were collected from developing inflorescence and RNA was extracted from the tissues samples of individual plants as described (Wang et al., 1995). The samples were prepared the same way for transgenic *Arabidopsis* plants displaying altered petal and anther phenotypes and for control wild type plants with normal petal and anther development. The RNA blotting and hybridization were performed as described above. The results from northern analysis of ICK1 expression showed that the transgenic plants which had altered petal and anther development also had a higher level of ICK1 expression in the young floral buds that the control wild type plants. Similar results were obtained from using both the first generation (T1) and the second generation (T2) transgenic plant.

Effect of ICK1 on differentiated cells such as pollen: Expression of ICK1 can be directed to more differentiated cells such as pollen, to determine its effect on differentiated cells to compare the effect on cells in proliferative tissue such as stamen primordia. As an example, transgenic plants were obtained using Bgp1-ICK1 chimeric gene construct. Eighteen (18) such transgenic *Arabidopsis* plants were transferred to soil and grew to maturity. All showed normal development of flower and anthers, unlike transgenic plants with AP3-ICK1 construct most of which showed petal alteration and male sterility. The Bgp1-ICK1 plants all set seeds without artificial pollination. As Bgp1 promoter has been shown to be able to direct a high level of GUS (beta-glucuronidase) gene expression in the pollen and tapetum of transgenic *Arabidopsis* plants (Xu et al., 1993), the observation that no significant male sterility phenotype developed in transgenic Bgp1-ICK1 plants indicates that a differentiated cell such as pollen can tolerate a moderate level of ICK1 with no detrimental effect on its function.

Ploidy level (endoreduplication): In accordance with one aspect, the invention may provide methods to modify ploidy in plant tissues by expressing plant CDK inhibitors. To exemplify this aspect, the nuclear ploidy levels of transformed plant tissues were determined using flow cytometry. Fresh tissue from mature *Arabidopsis* leaves was placed in a 1.5 ml tube containing 150 µl of solution A of the High Resolution DNA kit-Type P (Partech Gmbh, Munster, Germany). Tissue was chopped and 1 ml of solution B containing DAPI (4',6-diamidino-2-phenylindole dihydrochloride) was added for staining of nuclei. The suspension was filtered through 30-µm mesh. The sample was left for 5 minutes before analysed using a Partec PA flow cytometer (Partech Gmbh, Germany). Typically, 3,000–5,000 nuclei in one sample were measured. For each line of plant, 5–8 individual plants were used for measurement. The average peak value for various peaks of DNA contents (2C, 4C, 8C etc) was obtained. Mature rosette leaves from wild type and transgenic T3 plants (37–38 day old) were analysed for the DNA content (ploidy level) of isolated nuclei by flow cytometry.

Results obtained using the foregoing methods are given in Table 2. The data from wild type *Arabidopsis* leaf tissue show a similar profile of nuclear DNA content as described by Galbraith et al (1991) with four major peaks at 2C, 4C, 8C and 16C levels, and a minor peak at 32C level. Decreased ploidy level was observed in transgenic lines expressing one of the plant CDK inhibitors ICK1, ICN2 or CDKICr (the CDK inhibitor from *Chenopodium rubrum*). The extent of modification varies with different transgenic lines. In a 35S-ICK1 line, there were only 2C and 4C peaks. No peaks at 8C, 16C and 32C levels were detected. Similarly, plant lines expressing ICN2 or CDKICr also show decreased levels of ploidy in comparison to control plants. The present results indicate that CDK inhibitors may be used to modify the ploidy level of plant cells and tissues.

Table 2 shows relative peak area values from histograms of flow cytometry data. The DNA content was determined using nuclei isolated from mature leaf tissues of Wt and transgenic plants expressing plant CDK inhibitors. An average for each peak was obtained from 5–8 individual plants measured and expressed relatively in percentage with a total value for all peaks at 100%.

| Plant type | Plant line | Relative peak area value of different DNA contents | | | | |
|---|---|---|---|---|---|---|
| | | 2C | 4C | 8C | 16C | 32C |
| Wt | Wt | 27.4 | 35.2 | 36.9 | 13.2 | 0.4 |
| 35S-ICK1 | 200-13 | 71.9 | 28.1 | 0 | 0 | 0 |
| 35S-ICN2 | 202-6 | 44.9 | 40.3 | 14.7 | 0 | 0 |
| | 203-25 | 56.1 | 32.7 | 7.9 | 1.3 | 0 |
| 35S-CDKICr | 197-21 | 51.1 | 41.9 | 7.0 | 0 | 0 |

Other Transgenic Plants: In accordance with alternative embodiments, a wide variety of CDK inhibitors may be used to modify a wide variety of plant species. As an example, transgenic *Brassica napus* plants were obtained with AP3-ICK1 construct. Some of the plants showed much reduced petal size and significant reduction in seed-setting, with one plant showing almost complete sterility. The transgenic *Brassica* phenotypes were consistent with the pattern of AP3 promoter-directed gene expression, i.e. stronger expression in petal and stamen primordia and possibly low levels of expression in the inner integument or ovule (Day et al., 1995). Of fifty-two primary transformants, four showed altered petal development while other transformed plants showed normal petal development and seed-setting. For plants showing poor seed-setting, seeds were obtained by crosses with non-transformed wild-type *B. napus* plants. The inheritance of the altered phenotype was evident in progeny plants. For example, seven of eight progeny plants from one original transformant continued to display the alterations in petal development and three of the eight plants had reduced seed-setting (fertility). Petal growth in early flowers was more significantly affected than in late flowers. Transgenic *B. carinata* plants were also obtained, and phenotypic changes in petal development, similar to transgenic *B. napus* plants, were observed. These results show clearly that ICK1 can function in a heterologous *Brassica* plant and can be used to modify the growth and development of specific tissues or organs.

As yet another example, transgenic *B. napus* plants were obtained with a chimeric gene construct consisting of the Bgp1 promoter and ICK1. Of over forty putative transformants obtained, four showed reduced seed setting. The degree of reduction varied from an amount of about half the seed-setting in normal plants (in term of number of seeds per pods) to nearly complete sterility. Northern blot analysis showed a strong expression of ICK1 in the anther of a transgenic plant with male sterile phenotype (see below), suggesting that although moderate to low levels of expression did not affect the fertility, a higher level of expression could result in a sterile phenotype. It is also noted that none of the 18 *Arabidopsis* transformants showed any sterile phenotype with this construct. The absence of sterility among *Arabidopsis* transformants could be attributed to the difference in gene expression mediated by the Bgp1 promoter in different species, indicating that routine experimentation may be necessary to identify suitable promoters, and other control elements, for use in alternative embodiments herein. For example, the Bgp1 promoter, which is from *B. rapa* (*B. campestris*) (Xu et al., 1993), may be more effective in activating transgenic ICK1 expression in *B. napus* than in *A. thaliana* plants. The results in *Brassica* are indicative of the fact that it may be desirable in alternative embodiments to select promoters that mediate very strong expression of the CDK inhibitor gene, such as ICK1, during pollen/anther development, in order to optimize the occurrence of sterility. In addition, it may be desirable in some embodiments to mediate expression of the CDK inhibitor gene, such as ICK1, at earlier stages of microspore development before and during the last mitosis and preferably before and during meiosis, in order to produce more male sterile transgenic plants.

The expression of ICK1 in transgenic *B. napus* plants was analysed by northern hybridization using $^{32}$P-labeled ICK1 cDNA as probe. The Bpg1 promoter has previously been shown to direct strong exogenous GUS reporter gene expression in pollen of *A. thaliana* and *Nicotiana tobacum* (Xu et al., 1993). This example illustrates expression analysis for transgenic *B. napus* plants harboring Bgp1-ICK1 constructs. RNA samples were isolated from the leaf and mature anthers of a transgenic plant showing sterility phenotype (significant reduction in seed-setting) and a control *B. napus* Westar plant. For each sample, 15 μg of RNA was loaded and separated by electrophoresis. RNA transfer and hybridization were performed as described. There were no significant levels of ICK1 expression in leaves of both transgenic and control plants as well as in the pollen of the control plant. However, as expected, a strong level of ICK1 expression was observed in anthers of the transgenic plant. These results indicate that the reduction in fertility is indeed associated with elevated expression in anthers of the transgenic plant.

As another example, ICK1 expression was analysed in plants transformed by AP3-ICK1 construct. One *B. napus* plant showed changes in petal development including absence of one to all four petals and smaller petals. RNA samples were isolated from the leaf, sepal, petal, anther and whole young flower of the transgenic plant and the control plant. The only significant ICK1 expression was shown to be in the petals of the transgenic plants. There was no detectable signal under the conditions used for the tissues from the control plant. These data suggest that the phenotype observed in transgenic *Brasssica* plants was due to over-expression of ICK1 in petals.

In alternative embodiments, other plant CDK inhibitors may be used in transgenic or transient expression for regulating plant or plant cell growth and development. An example is described here.

A cDNA clone CDKI1 (AJ002173, SEQ ID No. 15 and SEQ ID No.16) sharing some sequence similarity with ICK1, ICK2, ICN2, ICN6 and ICN7 (Table 2) was identified from *Chenopodium rubrum* (by Fountain, Renz and Beck, with information available through NCBI internet databases). *C. rubrum* seeds were collected in Saskatchewan, Canada. RNA was isolated from seedlings and leaves. The full-length coding region of CDKI1 cDNA was cloned using RNA RT-PCR. The amplified fragment was cloned in sense orientation with a constitutive promoter and sequenced. The sequence data showed that the cloned cDNA was identical to CDKI1 of *C. rubrum* in the database. The *Agrobacterium* strain harboring an expression construct of CDKI1 was used to transform *Arabidopsis*. Selection for transformants was performed as described elsewhere herein. Significant morphological changes in plant development were observed in over one third of 38 transformants. These results indicate that the expression of *C. rubrum* CDKI1 may modify the growth and development of *Arabidopsis thaliana*. *Chenopodium* and *Arabidopsis* are phylogenetically rather distant species with Chenopodium belonging to the subclass of Caryophyllidae and *Arabidopsis* to the subclass Dilleniidae. The observation that a *Chenopodium* CDK inhibitor functions in *Arabidopsis* in the context of the present invention indicates that diverse plant CDK inhibitors may be used in various aspects of the present invention. Similarly, ICN2 has been used to transform *A. thaliana* to modify growth and development of that plant, producing transformed plants with distinct phenotypes. Thus, diverse CDK inhibitors may be used in accordance with various aspects of the invention.

TABLE 2

Percent Identity, using Clustal method with PAM250 residue weight table

| ICK1 | ICK2 | ICN2 | ICN6 | ICN7 | CDKI1 | |
|------|------|------|------|------|-------|------|
| 100  | 24.3 | 22.4 | 24.5 | 27.0 | 23.4  | ICK1 |
|      | 100  | 20.3 | 19.2 | 21.9 | 20.3  | ICK2 |
|      |      | 100  | 33.7 | 27.7 | 21.9  | ICN2 |
|      |      |      | 100  | 30.7 | 23.5  | ICN6 |
|      |      |      |      | 100  | 28.5  | ICN7 |
|      |      |      |      |      | 100   | CDKI1 |

Interaction of ICK1 with other proteins: CDK inhibitors may be used in various aspects of the invention to interact with a variety of regulatory components, such as other cell cycle proteins. For example, in some embodiments, it may be desirable to target a known regulatory moiety with a CDK inhibitor. Accordingly, in one aspect, an assay is provided to determine if a CDK inhibitor interacts with a known protein. Such interactions may be analyzed by a variety of assays for protein-protein interactions including the yeast two-hybrid assay (e.g. Phizicky and Fields, 1995; Malmqvist and Karlsson, 1997). For example, the full-length cDNA of the gene to be analyzed may be cloned in a GAL4-binding domain vector (Kohalmi et al., 1997) using PCR and gene specific primers with flanking restriction sites. Such constructs may be used to transform the yeast carrying the CDK inhibitor of interest, such as ICK1 in a GAL4-activation domain vector. Using this approach, for example, the interactions of ICK1 with a number of cell cycle-related genes from *A. thaliana* were examined (Table 3). In these examples, the yeast two-hybrid assay results indicate that in particular embodiments, ICK1 protein may interact with Cdc2a but not with Cdc2b. Similarly, ICK1 may interact with D-class cyclins, CycD1, CycD2 and CycD3, while not interacting with A/B-class mitotic cyclins, CycA2, CycB1 and CycB2 (Table 3). The yeast two-hybrid assay results also indicate that ICK1 may not interact in some embodiments with PCNA, also a cell cycle protein, and ATMAP2, a kinase sharing some similarity with Cdc2 kinase. Results such as these, indicating that ICK1 interacts with the G1 cyclins and Cdc2a but not the mitotic cyclins and Cdc2b, indicate that a CDK inhibitor, such as ICK1, may in some embodiments be used in the regulation of cell cycle initiation during plant growth and differentiation.

TABLE 3

Analyses of ICK1 interactions with other proteins in the yeast two-hybrid system

| Gene Group Examined | Gene in DB-Vector | Old Name | Interaction with ICK1 | |
|---|---|---|---|---|
| | | | Filter assay[1] | Quantification[2] |
| Control | vector alone | | − | 0 |
| Cdc2 kinase | cdc2a | | +++ | 2.65 |
| | cdc2b | | − | 0 |
| cyclin | cycD1;1 | Cyclin δ1 | +++ | 3.13 |
| | cycD2;1 | Cyclin δ2 | ++++ | 14.80 |
| | cycD3;1 | Cyclin δ3 | +++++ | 22.70 |
| | cycA2;2 | Cyc3bAt | − | 0.03 |
| | cycB1;1 | Cyc1At | − | 0.06 |
| | cycB2;2 | Cyc2bAt | − | 0.05 |
| PCNA | PCNAAt | | − | 0 |
| MAP kinase | ATMAP2 | | − | 0 |

Other plant CDK inhibitors: Other plant CDK inhibitors and CDK inhibitor genes sharing functional and sequence similarity with ICK1 may be identified using an approach similar to the approach used to isolate ICK1, based for example on their interactions with either Arabidospis Cdc2a or a D-class cyclin (e.g. cyclin D3 or cyclin D2). The CDK inhibitors identified in screens using Cdc2a are designated herein as ICKs (for Interactors of Cdc2 Kinase) and those identified in screens using cyclins are designated ICNs (for Interactors of Cyclin). Some CDK inhibitors may be isolated independently from both types of screens. The sequences of ICK2 (SEQ ID NO: 6), ICN2 (SEQ ID NO: 7), ICN6 (SEQ ID NO: 8), and ICN7 (SEQ ID NO: 9) are shown in FIGS. 2 through 6. These genes share at least two functional properties with ICK1: First, all of these genes encode proteins able to interact with either Cdc2a or a D-class cyclin or both. Such interactions may enable them to regulate the activity of plant CDKs in alternative embodiments of the invention. Second, these ICK/ICN proteins all share some sequence similarity in the region of ICK1 that is functionally important in some embodiments for its interaction with Cdc2a and cyclin D3 (discussed above in the section on "domains for ICK1 interactions with Cdc2a and cyclin D3"). These homologous genes or proteins may be used in some embodiments, in a manner similar to ICK1, to modulate plant growth and development. One or more such genes or proteins may be used in some embodiments alone or in combination to provide temporal and spatial regulation of cell cycle initiation and progressing during plant development.

Although various embodiments are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. For example, additional plant cyclin-dependent kinase inhibitor genes useful in regulating morphogenesis may be disclosed using the screening methods of the invention, such genes may share functional homology with ICK1, while being sequence-divergent from ICK1. The examples herein are illustrative only of various aspects or embodiments of the invention.

REFERENCES

Ausubel F M, Brent R, Kingston R E, Moore D D, Seidman J G, Smith J A, Stuhl K. (1995) Current Protocols in Molecular Biology, Vols 1, 2 and 3.

Babic V, Datla R S, Scoles G J, Keller W A (1998) Development of an efficient Agrobacterium-mediated transformation system for Brassica carinata. Plant Cell Rep 17: 183–188

Bai C, Sen P, Hofmann K, Ma L, Goebl M, Harper J W, Elledge S J (1996) SKP1 connects cell cycle regulators to the ubiquitin proteolysis machinery through a novel motif, the F-box. Cell 86: 263–274

Bechtold N, Ellis J, Pelletier (1993) In planta Agrobacterium-mediated gene transfer by infiltration of adult Arabidopsis thaliana plants. C R Acad Sci Paris, Science de la vie/Life ciences 316: 1194–1199

Bell M H, Halford N G, Ormrod J C, Francis D (1993) Tobacco plants transformed with cdc25, a mitotic inducer gene from fission yeast. Plant Mol Biol 23: 445–451

Brock T G, Kaufman P B (1991) Growth regulators: an account of hormones and growth regulation. In Growth and Development. Plant Physiology, A Treatise, Volume 10. San Diego: Academic Press, pp. 277–340

Casaccia-Bonnefil P, Tikoo R, Kiyokawa H, Friedrich V Jr, Chao M V, Koff A (1997) Oligodendrocyte precursor differentiation is perturbed in the absence of the cyclin-dependent kinase inhibitor p27Kip1. Genes Dev 11: 2335–2346

Chevray P M, Nathans D (1992) Protein interaction cloning in yeast: identification of mammalian proteins that react with the leucine zipper of Jun. Proc Natl Acad Sci USA 89: 5789–5793

Day C D, Galgoci B F, Irish V F (1995) Genetic ablation of petal and stamen primordia to elucidate cell interactions during floral development. Development 121: 2887–2895

De Veylder L, Segers G, Glab N, Casteels P, Van Montagu M, Inzé D (1997) The Arabidopsis Cks1At protein binds the cyclin-dependent kinases Cdc2aAt and Cdc2bAt. FEBS Lett 412: 446–452

Deng C, Zhang P, Harper J W, Elledge S J, Leder P (1995) Mice lacking p21CIP1/WAF1 undergo normal development, but are defective in G1 checkpoint control. Cell 82: 675–684

Doerner P, Jorgensen J-E, You R, Steppuhn J, Lamb C (1996) Control of root growth and development by cyclin expression. Nature 380: 520–523

Durand B, Fero M L, Roberts J M, Raff M C. (1998) p27Kip1 alters the response of cells to mitogen and is part of a cell-intrinsic timer that arrests the cell cycle and initiates differentiation. Curr Biol 8: 431–440

Edwards K, Johnstone C, Thompson C (1991) A simple and rapid method for the preparation of plant genomic DNA for PCR analysis. Nucleic Acids Res 19: 1349

Evans M L (1984) Functions of hormones at the cellular level of organization. In Hormonal Regulation of Development II. Encyclopedia of Plant Physiology, New Series, Volume 10 (Scott T. K. ed.). Berlin: Springer-Verlag, pp. 22–79

Fero M L, Rivkin M, Tasch M, Porter P, Carow C E, Firpo E, Polyak K, Tsai L H, Broudy V, Perlmutter R M, Kaushansky K, Roberts J M (1996) A syndrome of multiorgan hyperplasia with features of gigantism, tumorigenesis, and female sterility in p27(Kip1)-deficient mice. Cell 85: 733–744

Ferreira P C G, Hemerly A S, de Almeida Engler J, Van Montagu M, Engler G, Inzé D (1994) Developmental expression of the *Arabidopsis* cyclin gene cyc1At. *Plant Cell* 6: 1763–1774

Ferreira P C G, Hemerly A S, Villarroel R, Van Montagu M, Inzé D (1991) The *Arabidopsis* functional homolog of the p34$^{cdc2}$ protein kinase. *Plant Cell* 3: 531–540

Fields S, Song, O-K (1989) A novel genetic system to detect protein-protein interactions. *Nature* 340: 245–246

Flores-Rozas H, Kelman Z, Dean F B, Pan Z-Q, Harper J W, Elledge S J, O'Donnell M, Hurwitz J (1994) Cdk-interating protein 1 directly binds with proliferating cell nuclear antigen and inhibits DNA replication catalyzed by the DNA polymerase $_\delta$ holoenzyme. *Proc Natl Acad Sci USA* 91: 8655–8659

Francis D, Halford N G (1995) The plant cell cycle. *Physiol Plant* 93: 365–374

Gorst J R, John P C L, Sek F J (1991) Levels of p34$^{cdc2}$-like protein in dividing, differentiating and dedifferentiating cells of carrot. *Planta* 185: 304–310

Grafi G, Larkins B A (1995) Endoreduplication in maize endosperm: involvement of M phase-promoting factor inhibition and induction of S phase-related kinases. *Science* 269: 1262–1264

Harper J W, Elledge S J (1996) Cdk inhibitors in development and cancer. *Curr Opin Genet Dev* 6: 56–64

Hemerly A S, Ferreira P C G, de Almeida Engler J, Van Montagu M, Engler G, Inzé D (1993) cdc2a expression in *Arabidopsis thaliana* is linked with competence for cell division. *Plant Cell* 5: 1711–1723

Hemerly A, de Almeida Engler J, Bergounioux C, Van Montagu M, Engler G, Inzé D, Ferreira P (1995) Dominant negative mutants of the Cdc2 kinase uncouple cell division from iterative plant development. *EMBO J* 14: 3925–3936

Hindley J, Phear G A (1984) Sequence of the cell division gene CDC2 from *Schizosaccharomyces pombe*: patterns of splicing and homology to protein kinases. *Gene* 31: 129–134

Hirayama T, Imajuku Y, Anai T, Matsui M, Oka A (1991) Identification of two cell-cycle-controlling cdc2 gene homologs in *Arabidopsis thaliana*. *Gene* 105: 159–165

Jacobs T W (1995) Cell cycle control. *Annu Rev Plant Physiol Plant Mol Biol* 46: 317–339

John P C L, Zhang K, Dong C, Diederich L, Wightman F (1993) p34$^{cdc2}$ related proteins in control of cell cycle progression, the switch between division and differentiation in tissue development, and stimulation of division by auxin and cytokinin. *Aust J Plant Physiol* 20: 503–526

Kiyokawa H, Kineman R D, Manova-Todorova K O, Soares V C, Hoffman E S, Ono M, Khanam D, Hayday A C, Frohman L A, Koff A (1996) Enhanced growth of mice lacking the cyclin-dependent kinase inhibitor function of p27(Kip1). *Cell* 85: 721–732

Kohalmi S E, Nowak J, Crosby W L (1997) The yeast two-hybrid system. In *Differentially Expressed Genes in Plants: A Bench Manual Manual* (Hansen E, Harper G, eds), London, Taylor & Francis, pp. 63–82

Koncz C, Schell J (1986) The promoter of $T_L$-DNA gene 5 controls the tissue-specific expression of chimeric genes carried by a novel type of *Agrobacterium* binary vector. *Mol Gen Genet* 204: 383–396

Lörincz A T, Reed S I (1984) Primary structure homology between the product of yeast cell division control gene CDC28 and vertebrate oncogenes. *Nature* 307: 183–185

Lees E (1995) Cyclin-dependent kinase regulation. *Curr Opin Cell Biol* 7: 773–780

Lohdi M A, Ye G-N, Weeden N, Reisch B I (1994) A simple and efficient method for DNA extraction from grapevine cultivars and Vitis species. *Plant Mol Biol Rep* 12: 6–13

Malmqvist M, Karlsson R (1997) Biomolecular interaction analysis: affinity biosensor technologies for functional analysis of proteins. *Curr Opin Chem Biol* 1: 378–83

Martinez M C, Jorgensen J E, Lawton M A, Lamb C J, Doerner P W (1992) Spatial pattern of cdc2 expression in relation to meristem activity and cell proliferation during plant development. *Proc Natl Acad Sci USA* 89: 7360–7364

Meyerowitz E M (1997) Genetic control of cell division patterns in developing plants. *Cell* 88: 299–308

Miao G-H, Hong Z, Verma D P S (1993) Two functional soybean genes encoding p34$^{cdc2}$ protein kinases are regulated by different plant developmental pathways *Proc Natl Acad Sci USA* 90: 943–947

Missero C, Di Cunto F, Kiyokawa H, Koff A, Dotto G P (1996) The absence of p21Cip1/WAF1 alters keratinocyte growth and differentiation and promotes ras-tumor progression. *Genes Dev* 10: 3065–3075

Mizoguchi T, Gotoh Y, Nishida E, Yamaguchi-Shinozaki K, Hayashida N, Iwasaki T, Kamada H, Shinozaki K (1994) Characterization of two cDNAs that encode MAP kinase homologues in *Arabidopsis thaliana* and analysis of the possible role of auxin in activating such kinase activities in cultured cells. *Plant J* 5: 111–122

Moloney M M, Walker J M, Sharma K K (1989) High efficiency transformation of *Brassica napus* using *Agrobacterium* vectors. *Plant Cell Rep* 8: 238–242

Nakayama K, Ishida N, Shirane M, Inomata A, Inoue T, Shishido N, Horii I, Loh D Y, Nakayama K (1996) Mice lacking p27(Kip1) display increased body size, multiple organ hyperplasia, retinal dysplasia, and pituitary tumors. *Cell* 85: 707–720

Nasmyth K, Hunt T (1993) Cell cycle. Dams and sluices. *Nature* 366: 634–635

Nilsson O, Wu E, Wolfe D S, Weigel D (1998) Genetic ablation of flowers in transgenic *Arabidopsis*. *Plant J* 15: 789–804

Newton R J (1977) Abscisic acid effects on fronds and roots of *Lemna minor* L. *Amer J Bot* 64: 45–49

Phizicky E M, Fields S (1995) Protein-protein interactions: methods for detection and analysis. *Microbiol Rev* 59: 94–123

Pines J (1995) Cyclins and cyclin-dependent kinases: a biochemical view. *Biochem J* 308: 697–711

Renaudin J-P, Doonan J H, Freeman D, Hashimoto J, Hirt H, Inzé D, Jacobs T, Kouchi H, Rouzé P, Sauter M, Savouré A, Sorrell D A, Sundaresan V, Murray JAH (1996) Plant Cyclins: a unified nomenclature for plant A-, B- and D-type cyclins based on sequence organization. *Plant Mol Biol* 32: 1003–1018

Reynolds A, Lundblad V (1994) Yeast vectors and assays for expression of cloned genes. In *Current Protocols in Molecular Biology* (Ausubel, F. M. et al, eds), New York, Wiley & Sons, pp. 13.6.1–13.6.4

Robertson J M, Yeung E C, Reid D M, Hubick K T (1990) Developmental responses to drought and abscisic acid in sunflower roots. 2. Mitotic activity. *J Exp Bot* 41: 339–350

Russo A A, Jeffrey P D, Patten A K, Massagué J, Pavletich N P (1996) Crystal structure of the p27Kip1 cyclin-dependent-kinase inhibitor bound to the cyclin A-Cdk2 complex. *Nature* 382: 325–331

Sauter M, Mekhedov S L, Kende H (1995) Gibberellin promotes histone H1 kinase activity and the expression of cdc2 and cyclin genes during the induction of rapid growth in deepwater rice internodes. *Plant J* 7: 623–632

Segers G, Gadisseur I, Bergounioux C, de Almeida Engler J, Jacqmard A, Van Montagu M, Inzé D (1996) The *Arabidopsis* cyclin-dependent kinase gene cdc2bAt is preferentially expressed during S and $G_2$ phases of the cell cycle. *Plant J* 10: 601–612

Sherr C J, Roberts J M (1995) Inhibitors of mammalian G1 cyclin-dependent kinases. *Genes Dev* 9: 1149–1163

Soni R, Carmichael J P, Shah Z H, Murray J A H (1995) A family of cyclin D homologs from plants differentially controlled by growth regulators and containing the conserved retinoblastoma protein interaction motif. *Plant Cell* 7: 85–103

Southern E M (1975) Detection of specific sequences among DNA fragments separated by gel electrophoresis. *J Mol Biol* 98: 503–517

Steward G R, Smith H (1972) Effects of abscisic acid on nuclei acid synthesis and the induction of nitrate reductase in *Lemna polyrhiza*. *J Exp Bot* 23Z: 875–885

Waga S, Hannon G J, Beach D, Stillman B (1994) The p21 inhibitor of cyclin-dependent kinases controls DNA replication by interaction with PCNA. *Nature* 369: 574–578

Wang H, Datla R, Georges F, Loewen M, Cutler A J (1995) Promoters from kin1 and cor6. 6, two homologous *Arabidopsis thaliana* genes: transcriptional regulation and gene expression induced by low temperature, ABA, osmoticum and dehydration. *Plant Mol Biol* 28: 605–617

Wang H, Fowke L C, Crosby W L (1997) A plant cyclin-dependent kinase inhibitor gene. *Nature* 386: 451–452

Wu H, Wade M, Krall L, Grisham J, Xiong Y, Van Dyke T (1996) Targeted in vivo expression of the cyclin-dependent kinase inhibitor p21 halts hepatocyte cell-cycle progression, postnatal liver development and regeneration. *Genes Dev* 10: 245–260

Xu H, Davies S P, Kwan B Y, O'Brien A P, Singh M, Knox R B (1993) Haploid and diploid expression of a *Brassica campestris* anther-specific gene promoter in *Arabidopsis* and tobacco. *Mol Gen Genet* 239: 58–65

Yan Y, Frisen J, Lee M H, Massague J, Barbacid M (1997) Ablation of the CDK inhibitor p57Kip2 results in increased apoptosis and delayed differentiation during mouse development. *Genes Dev* 11: 973–983

Zhang P, Liegeois N J, Wong C, Finegold M, Hou H, Thompson J C, Silverman A, Harper J W, DePinho R A, Elledge S J (1997) Altered cell differentiation and proliferation in mice lacking p57KIP2 indicates a role in Beckwith-Wiedemann syndrome. *Nature* 387: 151–158.

What is claimed is:

1. A method of modifying development of a plant comprising transforming a plant cell with a nucleic acid encoding a plant cyclin-dependent kinase inhibitor polypeptide to produce a transformed plant cell, wherein the nucleic acid comprises the nucleic acid sequence set forth in SEQ ID NO: 1, SEQ ID NO: 3, or a nucleic acid sequence having at least 95% sequence identity with the nucleic acid sequence set forth in SEQ ID NO: 1 or SEQ ID NO: 3; and, growing the transformed plant cell or progeny of the transformed plant cell to produce a transformed plant under conditions wherein the plant cyclin-dependent kinase inhibitor polypeptide is expressed in a proliferative tissue of the transformed plant to bind to a plant cyclin-dependant protein kinase or a plant cyclin to inhibit development of a differentiated tissue in the plant.

2. The method of claim 1, wherein the nucleic acid encoding the cyclin-dependent kinase inhibitor comprises the nucleic acid sequence set forth in SEQ ID NO: 1 or SEQ ID NO: 3.

3. The method of claim 1, wherein the cyclin-dependent kinase inhibitor polypeptide is comprises the amino acid sequence set forth in SEQ ID NO: 10.

4. The method of claim 1, wherein the plant is a member of the Cruciferae family.

5. The method of claim 1, wherein the plant is a member of the *Brassica* genus.

6. The method of claim 1, wherein the nucleic acid encoding the cyclin-dependent kinase inhibitor polypeptide is operably linked to a constitutive promoter.

7. The method of claim 1, wherein the nucleic acid encoding the cyclin-dependent kinase inhibitor polypeptide is operably linked to a tissue-specific promoter.

8. The method of claim 7, wherein the tissue-specific promoter is the AP3 promoter.

9. The method of claim 7, wherein the tissue-specific promoter mediates expression of the nucleic acid encoding the cyclin-dependent kinase inhibitor polypeptide in petal or stamen primordia.

10. The method of claim 1 wherein modifying development of the plant makes the plant male sterile.

11. The method of claim 1 wherein the development of the tissue in the plant is modified so that petals on the transformed plant are altered or absent.

12. The method of claim 1, wherein the nucleic acid encoding the cyclin-dependent kinase inhibitor comprises:

a nucleic acid sequence having at least 95% sequence identity with a nucleic acid sequence set forth in SEQ ID NO: 1 or SEQ ID NO: 3.

13. The method of claim 1, wherein the nucleic acid encoding the cyclin-dependent kinase inhibitor comprises a nucleic acid sequence as set forth in SEQ ID NO: 1 or 3.

14. A method of modifying floral development of a plant, comprising:

transforming a plant cell with a nucleic acid encoding an *Arabidopsis* cyclin-dependent kinase inhibitor polypeptide encoded by a nucleic acid comprising:

a nucleic acid sequence as set forth in SEQ ID NO: 1;

a nucleic acid sequence as set forth in SEQ ID NO: 3; or a nucleic acid sequence having at least 95% sequence identity with a nucleic acid sequence set forth in SEQ ID NO: 1 or SEQ ID NO: 3 to produce a transformed plant cell; and growing the transformed plant cell or progeny of the transformed plant cell to produce a transformed plant, wherein the plant cyclin-dependent kinase inhibitor polypeptide is expressed in petal or stamen primordia of the transformed plant to inhibit floral development.

15. A method of modifying development of a plant, comprising:
    transforming a plant cell with a nucleic acid encoding an *Arabidopsis* cyclin-dependent kinase inhibitor polypeptide encoded by a nucleic acid comprising:
    a nucleic acid sequence as set forth in SEQ ID NO: 1;
    a nucleic acid sequence as set forth in SEQ ID NO: 3; or
    a nucleic acid sequence having at least 95% sequence identity with a nucleic acid sequence set forth in SEQ ID NO: 1 or SEQ ID NO: 3 and
    growing the transformed plant cell or progeny of the transformed plant cell to produce a transformed plant,
wherein expression of the plant cyclin-dependent kinase inhibitor polypeptide decreases ploidy of a differentiated tissue in the plant.

16. A method of modifying development of a plant, comprising:
    transforming a plant cell with a nucleic acid encoding the amino acid sequence set forth in SEQ ID NO: 10 to produce a transformed plant cell; and
    growing the transformed plant cell or progeny of the transformed plant cell to produce a transformed plant,
wherein (a) the encoded polypeptide is expressed in petal and/or stamen primordia of the transformed plant, and the modified development of the plant comprises inhibition of floral development; or (b) the encoded polypeptide is expressed in leaf cells of the transformed plant, and the modified development of the plant comprises a decrease in ploidy.

* * * * *

UNITED STATES PATENT AND TRADEMARK OFFICE
CERTIFICATE OF CORRECTION

PATENT NO.        : 7,078,591 B2                                  Page 1 of 1
APPLICATION NO.   : 09/733507
DATED             : July 18, 2006
INVENTOR(S)       : Wang et al.

It is certified that error appears in the above-identified patent and that said Letters Patent is hereby corrected as shown below:

On Title Page of the Patent:

In section (73) Assignees: "Her Majessty the Queen in right of Canada, as represented by the Minister of Natural Resources ..." should be --Her Majesty the Queen in right of Canada, as represented by the Minister of Agriculture and Agri-Food--.

Also in section (73) Assignees: "The Natural Research Counsel of Canada ..." should be -- The National Research Counsel of Canada --.

Col. 43

In the Claims:

In line 55 of Claim 3, "...polypeptide is comprises..." should be --...polypeptide comprises...--.

Signed and Sealed this

Twenty-sixth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,078,591 B2  Page 1 of 1
APPLICATION NO. : 09/733507
DATED : July 18, 2006
INVENTOR(S) : Wang et al.

It is certified that error appears in the above-identified patent and that said Letters Patent is hereby corrected as shown below:

On Cover Page of Patent:

Under section (63) "Related U.S. Application Data", section (30) "Foreign Application Priority Data" is missing. Item (30) should read --(30)      Foreign Application Priority Data
  Jun. 8, 1998     (CA) .......................................... 2235978
  Dec. 31, 1998    (CA) .......................................... 2256121--

Signed and Sealed this
Twenty-sixth Day of July, 2011

David J. Kappos
*Director of the United States Patent and Trademark Office*